US008017938B2

(12) United States Patent
Gomez et al.

(10) Patent No.: US 8,017,938 B2
(45) Date of Patent: Sep. 13, 2011

(54) APPARATUS FOR MICROARRAY BINDING SENSORS HAVING BIOLOGICAL PROBE MATERIALS USING CARBON NANOTUBE TRANSISTORS

(75) Inventors: Romel Del Rosario Gomez, Silver Spring, MD (US); Javed Khan, Derwood, MD (US); Herman Pandana, Lanham, MD (US); Konrad Aschenbach, Laurel, MD (US); Michael Fuhrer, Hyattsville, MD (US); Jun Stephen Wei, Gaithersburg, MD (US)

(73) Assignees: The United States of America as represented by the Department of Health and Human Services, Washington, DC (US); University of Maryland, College Park, College Park, MD (US)

( * ) Notice: Subject to any disclaimer, the term of this patent is extended or adjusted under 35 U.S.C. 154(b) by 1125 days.

(21) Appl. No.: 11/723,369

(22) Filed: Mar. 19, 2007

(65) Prior Publication Data
US 2008/0035494 A1  Feb. 14, 2008

Related U.S. Application Data

(60) Provisional application No. 60/743,524, filed on Mar. 17, 2006.

(51) Int. Cl.
*H01L 51/10* (2006.01)
*H01L 51/30* (2006.01)

(52) U.S. Cl. .................... 257/40; 257/E51.04; 977/702; 977/920; 977/938

(58) Field of Classification Search ............... 257/9, 20, 257/40, E51.001, E51.002, E51.003, E51.004, 257/E51.005, E51.006, E51.023, E51.024, 257/E51.025, E51.026, E51.038, E51.039, 257/E51.04; 977/700, 701, 702, 703, 704, 977/705, 706, 785, 920, 921, 922, 936, 938
See application file for complete search history.

(56) References Cited

U.S. PATENT DOCUMENTS

| | | | |
|---|---|---|---|
| 2002/0117659 A1 | 8/2002 | Lieber et al. | 257/14 |
| 2005/0112052 A1 | 5/2005 | Gu et al. | 423/447.1 |
| 2006/0199193 A1 | 9/2006 | Koo et al. | 435/6 |
| 2006/0246497 A1 | 11/2006 | Huang et al. | 435/6 |

FOREIGN PATENT DOCUMENTS

| | | |
|---|---|---|
| WO | WO 2005/000735 A2 | 1/2005 |
| WO | WO 2006/024023 A2 | 3/2006 |

OTHER PUBLICATIONS

International Search Report and Written Opinion of the ISA for PCT/US2007/006809, mailed on Aug. 23, 2007.

*Primary Examiner* — Samuel Gebremariam
*Assistant Examiner* — Andrew O Arena
(74) *Attorney, Agent, or Firm* — Polsinelli Shughart PC; Teddy C. Scott, Jr.; Paul A. Jenny

(57) ABSTRACT

A microarray apparatus is provided which contains at least one chip having source and drain electrodes positioned on an array of carbon nanotube transistors which allows for electronic detection of nucleic acid hybridizations, thereby affording both increased sensitivity and the capability of miniaturization.

28 Claims, 14 Drawing Sheets

US 8,017,938 B2

APPARATUS FOR MICROARRAY BINDING SENSORS HAVING BIOLOGICAL PROBE MATERIALS USING CARBON NANOTUBE TRANSISTORS

CROSS REFERENCE TO RELATED CASES

This application claims the benefit of Provisional U.S. Application Ser. No. 60/743,524, filed Mar. 17, 2006, which is incorporated by reference herein in its entirety.

STATEMENT REGARDING FEDERALLY SPONSORED RESEARCH

The work leading up to the present invention was funded, at least in part, by NSA under Grant H9823004C0470. As such, the U.S. Government may have certain rights in the present invention under the provisions of 35 U.S.C. 203 et seq.

BACKGROUND OF THE INVENTION

1. Field of the Invention

The present invention relates to an apparatus containing microarray binding sensors having biological probe materials using carbon nanotube transistors and various methods for detecting binding of biological target materials thereto.

2. Description of the Background

DNA microarrays are powerful tools in molecular biology, and generally contain an array of hundreds to tens of thousands of genes spotted on a solid substrate, and which is used to identify and quantify unknown gene samples. The microarray technique is predicated upon the property that nucleic acid hybridization is highly specific, i.e., cytosine binds only to guanine and thymine to adenine. Thus, a specific sequence of nucleic acids, for example, 5' ATCATC3,' will preferentially bind with its complementary sequence, 3' TAGTAG5.'

DNA microarrays are invaluable techniques for high throughput monitoring of gene expression at the transcription level, determining genome wide DNA copy number changes, identifying targets of transcription factors, sequencing and, more recently, for profiling micro RNA (miRNA) levels in cancer. The central dogma in molecular biology is that DNA is transcribed to ribonucleic acid (RNA), and the information in the RNA is used to make proteins, by a process called translation. Since the function and metabolism of the cell is regulated by the protein produced in the cell, many diseases caused by gene mutations, such as cancers, can be studied by monitoring the gene expression. Thus, the identification and quantification of genes is of particular interest. It is important to know the particular gene or genes that contribute to a certain phenotype, and also the amount of the gene that signifies the level of the gene expression. There are diseases, however, which are not necessarily caused by gene mutation or change in DNA sequence, but which are caused by an abnormal amount of the gene or abnormal level of gene expression. High throughput gene identification enables researchers to quickly identify the genes that undergo mutations in a certain disease. Comparative gene expression compares the level of gene expression, between a cancerous cell and a healthy cell, for example. In a typical DNA microarray experiment that relies on fluorescent detection, comparative gene expression is done by labeling the genes in one cell with one color of fluorescent reporter molecules, and genes in the other cell with another. The relative intensity of each color is a direct measure of the abundance of the genes from the two cells. Given the versatility of DNA microarrays, the impact thereof on healthcare is expected to be quite significant if DNA microarrays can be deployed widely and inexpensively. It will enable rapid diagnosis of diseases, as well as enable drugs to be tailored to each patient to achieve highest effectiveness.

The first reported DNA microarray was fabricated on nylon membranes using cDNA clones and utilized radioactively labeled targets for detection. Since then, many large-scale DNA microarray platforms have been developed, which have included, double-stranded cDNA, single stranded short 25mers (Affymetrix), mid-sized 30mer (Combimatrix) or long 50-70mers (Nimblegen or Agilent) oligonucleotides. All of these methods rely upon various combinations of enzymatic amplification of the nucleic acid and fluorescent labeling of targets, hybridization, and amplification of signal followed by detection by optical scanners.

In a microarray experiment, an array of known single stranded DNA sequences, called probes, is immobilized on a substrate and later exposed to an unknown set of target genes (or single stranded DNA sequences) that have been chemically tagged with fluorescent molecules. In places on the array where the probe and target sequences are complementary, hybridization occurs and the locations of these specific binding events are reported by the fluorescent molecules.

A major hurdle of using DNA microarray as a clinical tool is that the technique is laborious, requires complex protocols, requires large amounts of reagents, and suffers from low signal to noise ratio and rapid optical degradation. While significant strides have been made in fluorescent-based DNA microarray technology, the methodologies are often time-consuming and in addition rely on the determination of fluorescence intensity and the sensitivity is thus limited by the ability to detect small numbers of photons. Moreover, fluorescent molecules suffer from photobleaching, which means that the fluorescent molecule will stop to fluoresce after receiving a certain amount of excitation.

A variety of DNA detection schemes has been reported in the literature. The detection mechanisms involve detection of the existence of the reporter molecules or tags, such as radio-isotopes, fluorophores, quantum dots, gold nanoparticles, magnetic nanoparticles, or enzymes, for example. A brief survey of known fluorescent based DNA microarray, and other label-free electronic field effect DNA detection schemes is described below in subsections 1) and 2).

1. Fluorescence-Based Microarrays

Typically, microarrays are microscope glass slides spotted with thousands of different genes. The array does not have built-in reader. The detection is performed using a fluorescence scanner after hybridization with fluorescent-tagged target DNA. There are two ways to make microarrays: (i) spotting cDNA or oligonucleotides onto the substrate with a robotic spotter, or (ii) direct oligonucleotide synthesis on the solid support. A robotic spotter uses thousands of capillary pins dipped into wells containing different kind of genes and transports the genes onto a functionalized solid substrate to create gene spots. Another approach, such as the one employed by affymetrix, uses direct oligonucleotide synthesis on the substrate. The ingredients are solutions of the four nucleotides: adenine, guanine, cytosine and thymine which bear light sensitive protecting group. The process starts with a quartz wafer that is coated with a light-sensitive chemical compound that prevents coupling between the wafer and the first nucleotide of the DNA probe being created. Lithographic masks are used to either block or transmit light onto specific locations of the wafer surface. The exposed spots are now ready to couple with a nucleotide. The surface is then flooded with a solution containing either adenine, thymine, cytosine, or guanine, and coupling occurs only in those regions on the glass that have been deprotected through illumination. The coupled nucleotide also bears a light-sensitive protecting group, so the cycle of deprotection and coupling until the probes reach their full length, usually 25 nucleotides.

2. Field Effect DNA Detection

In general, many field effect based biomolecule detection schemes resemble the structure of ISFET (ion sensitive field effect transistor), which was first introduced by Bergveld in 1970. *IEEE Transactions on Biomedical Engineering*, 17(1): 70-71 (1970). ISFET is similar to the conventional MOSFET (metal oxide semiconductor field effect transistor), except that the metal layer is replace by an ion-sensitive membrane, an electrolyte solution and a counter electrode. EISFET (electrolyte-insulator-silicon FET) is another acronym that refers to the same structure. The drain source current is modulated by field effect from the ions that can reach the oxide. ISFET technology has been so well-developed that it has made its way to the market as pH meters. Souteyrand et al. is the first to demonstrate label-free-homo-oligomer DNA (18-mer and 1000-mer of poly(dA)DNA) hybridization detection using silicon ISFET. *Journal Physical Chemistry B*, 101(15): 2980-2985 (1997). They observed a shift in the flat-band potential of the underlying semiconductor in response to the increase of surface charges induced by hybridization between the complementary homo-oligomer strands. Several other papers demonstrating successful field effect DNA detection using silicon ISFET structure are mentioned below. Pouthas et al. demonstrated field effect detection of 5 µM, 10 µM, 20 µM of 20-mer oligonucleotide and emphasized the need for low ionic buffer. *Physical Review E*, 70(3): 031906 (2004). Fritz et al. were able to detect in real time as dilute as 2 nM of 12-mer oligonucleotide. Proceedings of the National Academy of Science USA, 99(22): 14142-14146. They utilized poly L-lyssine (PLL) to immobilize the probe DNA, and claimed that real time rapid hybridization at low ionic buffer (23 mM phosphate buffer) was enable by the positively charged PLL surface that compensated for electrostatic repulsion between complementary DNA strands. Peckerar et al. demonstrated detection of 1 fM 15-mer DNA. *IEEE Circuits & Davies Magazine* 19(2): 17-24 (2003).

Thus, current methods for detecting DNA rely upon various combinations of enzymatic amplification of nucleic acids and fluorescent labeling of targets, which entail enzymatic manipulation of the nucleic acid being tested and chemical labeling, respectively. These methods are both time consuming and afford limited sensitivity.

Further, while more recently, DNA microarray technology has been deployed as a tool for monitoring gene expression patterns and profiling of micro RNA (miRNA) in normal and cancerous tissue, quantification of changes has typically been optically-based. While this technique is highly sensitive, use of optical methods impedes progress in both system miniaturization and in direct interfacing with data collection electronics.

Hence, a need exists for a method of detecting DNA that overcomes these disadvantages.

SUMMARY OF THE INVENTION

Accordingly, it is an object of the present invention to provide an apparatus for microarray binding sensors having biological probe materials using carbon nanotube transistors.

It is a more particular object of the present invention to provide such an apparatus containing at least one chip, each being positioned on an array of carbon nanotube transistors on an insulating substrate and covered by a thin insulating oxide or nitride with exposed metallic terminals.

It is, moreover, another object of the present invention to provide a method of electronically detecting binding of biological probe materials to target materials therefor.

It is also an object of the present invention to provide a method for electronically detecting oligonucleotide-oligonucleotide binding.

It is further an object of the present invention to provide a method of forming iron nanoparticle catalysts for carbon nanotube growth.

Additionally, it is an object of the present invention to provide a process for preparing an insulating gate material to afford transistors having improved conductance.

It is, moreover, an object of the present invention to provide a method of oligonucleotide immobilization.

Further, it is an object of the present invention to provide a method of electronically detecting biological materials using bound aptamers.

It is, in addition, an object of the present invention to provide a method of measuring signal variation as a function of target material concentration, as well as a method of electronically determining relative abundances of specific target materials.

The above objects and others are provided by an apparatus containing:

(a) at least one chip, incorporating an array of carbon nanotube transistors on an insulating substrate and covered by a thin insulating oxide or nitride with exposed metallic terminals, (b) a conducting metal to provide electrical conductivity to the exposed transistor terminals, (c) a multiplicity of specific biological probe materials attached on the insulating oxide or nitride layer, (d) a microfluidic channel above the insulating oxide or nitride layer to direct flow of liquid solutions containing biological material;

(e) electronic circuitry configured to detect change in electrical charge due to binding of the biological probe materials to target materials in the biological material of step d), (f) means configured to quantitatively correlate detected change in electrical charge from e) into an amount of bound target material, and (g) an automated sensing means configured to determine a relative abundance of specific target materials using the electronic circuitry of e) and the means of f).

DETAILED DESCRIPTION OF THE PREFERRED EMBODIMENTS

The present invention is predicated, at least in part, upon the provision of a highly sensitive apparatus based on carbon nanotube transistors for the electronic detection of biological probe-target binding. In accordance with the present invention, a single carbon nanotube transistor (CNT) is associated with a distinct biological probe material, thereby far surpassing existing technology in sensitivity, ease of use and capability of miniaturization. Importantly, the present apparatus offers a significant advantage in simplicity of protocol as the method used therewith does not require chemical or enzymatic manipulation of the target being detected.

Further, the present invention does not rely upon optical detection means so that the present apparatus can be miniaturized. Rather, the present invention provides, in part, a fabricated nanoplatform using field-effect transistor (FET) sensing with a gate terminal of the FET functionalized with an biological probe material of interest. While either carbon nanotubes or silicon nanowires may be used as FET, carbon nanotubes are preferred.

The present invention, thus, provides an apparatus for biological target material detection which uses an array of carbon nanotube transistors, with each being operated as a field effect transistor. The current versus voltage characteristics or transconductance between the source and drain electrodes is measured before and after a binding event between the biological probe and target materials. By using a mathematical relationship, the exact amount of target binding can be extracted. The present apparatus employs peripheral electronic networks and amplifiers and measurement algorithms to perform a highly quantitatively measure of the amount of binding of the biological probe-target materials. The data is calibrated using well known techniques familiar to artisans in molecular biology. Thus, the present invention may be used for the same purposes as conventional DNA microarrays but with the aforementioned advantages, such as increased sensitivity but without chemical or enzymatic manipulation of the nucleic acids being detected.

Figure 1:
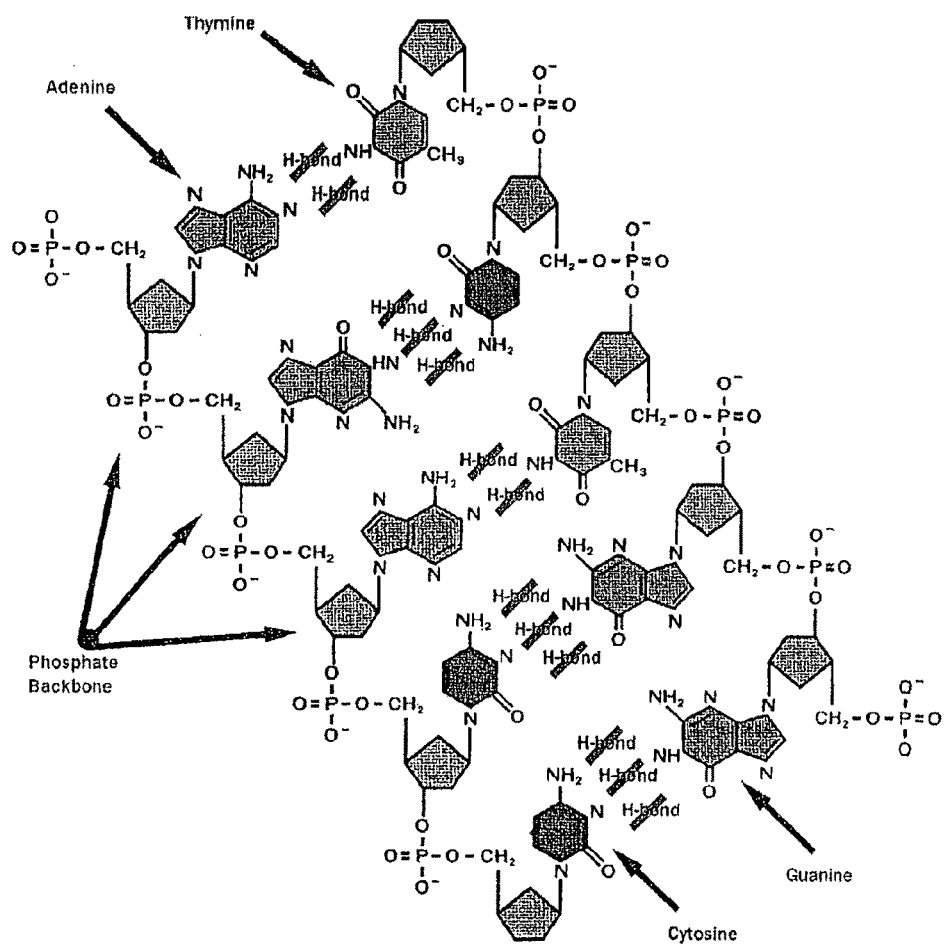
FIG. 1 illustrates the structure of double stranded DNA bonded by hydrogen bonding. Electronic detection of DNA, for example, is possible as the phosphate backbone of the DNA is charged when ionized or dissolved in solution.

The difference in current versus voltage characteristics or transconductance between the source and drain electrodes before and after a binding, such as an hybridization event, arises from the known fact that the binding of an oligonucleotide, for example, such as a target DNA, to a complementary sequence of another chain of nucleic acid, termed a probe, in a sequence specific manner results in a total charge change on the probe. This may be appreciated from FIG. 1, which shows the occurrences of hydrogen bonds in base pairing (two hydrogen bonds in an adenine (A)-thymine (T) pair, and three in a cytosine (C)-guanine (G) pair), and negative charges carried by the phosphate backbone.

The apparatus of the present invention is advantageous as it can be miniaturized and the methodologies of using the apparatus exhibit at least five major advantages for detecting DNA, which are:

(i) since the apparatus detects charge, the sample does not need a labeling step, whereby the process is less laborious;

(ii) since the methodology is label-free, the sensitivity is better than the fluorescent detection scheme, because in fluorescent detection schemes, the sensitivity depends both on the photodetector and the completeness of the fluorescent tagging;

(iii) the methodology does not suffer from photobleaching, and the apparatus can be used for detection many times if time averaging is needed;

(iv) application of electric field can increase the hybridization reaction rate, which increases the throughput of the assay; and (v) the methodology does not use optical detection means, thus facilitating miniaturization.

The method described in detail below allows for the sensitive and specific detection of nucleic acid hybridization without the need of for extensive chemical or enzymatic manipulation of the DNA or RNA. The applications of the present apparatus and methodologies using the same are extensive. A few may be mentioned:

1. Monitoring Gene expression: research and for diagnostics and predicting prognosis
2. Monitoring micro RNA (miRNA) expressions, (MicroRNAs (miRNAs) are small, RNA molecules encoded in the genomes of plants and animals. These highly conserved, -21-mer RNAs regulate the expression of genes by binding to the anywhere along the mRNA but particularly the 3'-untranslated regions (3'-UTR) of specific mRNAs. They have been reported to be differentially expressed in cancers of specific types and there is evidence that certain profiles may predict the patient outcome in cancer.
3. Detecting DNA copy number changes, performing electronic comparative genomic hybridization, detecting deletions in chromosomal regions.
4. Sequencing entire genes, may replace the current gel based sequencing techniques.
5. Single Nucleotide Polymorphism detection.
6. Detecting pathogens in the air, blood and body secretions.

DEFINITIONS

As used herein, the following terms are defined as follows:

APTAMER: an oligonucleotide or peptide that binds a specific target molecule. These oligonucleotide and/or peptides have been engineered through in vitro selection or equivalently SELEX (systematic evolution of ligands by exponential enrichment) to bind to various molecular targets such as small molecules, proteins, nucleic acids, and even cells, tissues and organisms. Aptamers often molecule recognition properties that rival antibodies.

CARBON NANOTUBE: A one-atom thick of graphite (called graphene) rolled up into a seamless cylinder with a diameter on the order of a nanometer (nm). The length-to-diameter ratio may be in excess of 10,000. Carbon nanotubes (CNT) may be either single-walled (SWNT) or multi-walled (MWNT).

MICROARRAY: This refers to, in the case of DNA for example, a collection of DNA spots attached to a solid surface, such as glass, plastic or silicon chip. The affixed DNA spots are often referred to as probes or reporters. Microarrays may be fabricated using a variety of techniques, such as photolithography using ink-jet printing.

OLIGONUCLEOTIDE: A nucleotide sequence of either DNA or RNA. The length of a base sequence is often denoted by 'mer'. Thus, a fragment of 15 bases called a 15-mer.

MICROFLUIDIC CHANNEL: A channel having at least one dimension of less than 1 nm. Common fluids used in microfluidic devices and channels thereof are blood samples, bacterial cell suspension, and protein or antibody solutions, for example. The volume of fluids within these channels is on the order of a few nanoliters (nl).

PROBE (OR PROBE MATERIAL): Any biological material having the ability to bind to a target material. Examples include segments of DNA, RNA, and oligonucleotides and polynucleotides, generally; cell receptors or viruses. As most commonly used, the term refers specifically to segments of single-stranded DNA or RNA having the ability to bind or hybridize, and thereby detect, complementary sequences in the presence of large amount of non-complementary DNA and RNA, respectively.

TARGET (or TARGET MATERIAL): Any biological material having the ability to bind to a probe material by hybridization, for example.

Figure 9:
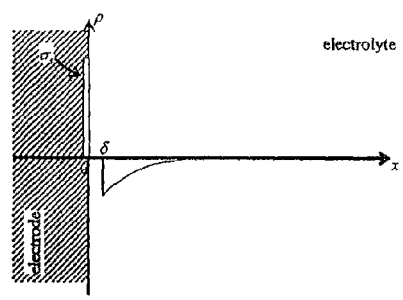
FIG. 9 illustrates an interface of an electrode in an electrolyte showing positive surface charges as the electrode and the diffused ions in the outer Helmholtz layer (x>δ).

Terms in Figures:

In FIG. 9:

x. horizontal axis of the figure, drawn perpendicularly to the electrode-electrolyte, indicating distance away from the interface.

$\rho$: the vertical axis of the figure to describe the profile of the electrical charge density, arising from the immobilized DNA molecules and rearrangement of ions in the buffer solution 0: the origin of the axes, denotes oxide-electrolyte interface $\sigma_s$: the surface charge density of the immobilized DNA molecules to the electrode-electrolyte interface.

$\delta$: the closest distance from the electrode-electrolyte interface a solvated ion can approach.

Figure 10:
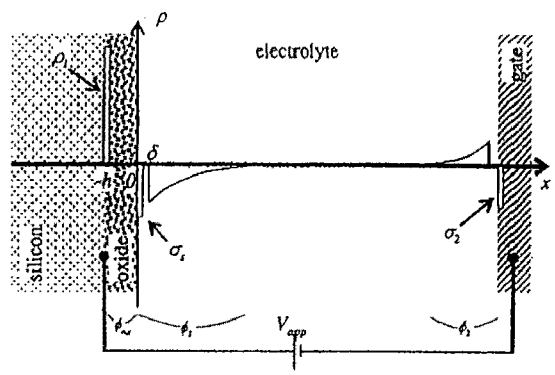
FIG. 10 illustrates charge distribution among various interfaces.

In FIG. 10:

x. horizontal axis of the figure, drawn perpendicular to the electrode-electrolyte interface, indicating distance away from the interface;

$\rho$: the vertical axis of the figure to describe the profile of the electrical charge density arising from the immobilized DNA molecules and rearrangement of ions in the buffer solution 0: origin of the x-axis, denoting oxide-electrolyte interface.

−h is the distance from the oxide-electrolyte interface to the silicon-oxide interface h: denotes the thickness of the oxide.

$\sigma_s$: the surface charge density of the immobilized DNA molecules to the electrode-electrolyte interface.

$\delta$: the closest distance from the electrode-electrolyte interface a solvated ion can approach.

$\rho_l$: the charge density induced in the carbon nanotube.

$\sigma_2$: the surface charge density induced in the gate electrode.

$\phi_{ox}$: the voltage drop across the oxide.

$\phi_1$: the voltage drop across the oxide-electrolyte interface $\phi_2$: the voltage drop across the electrolyte-gate interface.

$V_{app}$: the applied voltage to the gate and silicon, required to maintained a fixed charge density on the carbon nanotube, such that a fixed electrical current is flowing through the carbon nanotube.

Figure 11:
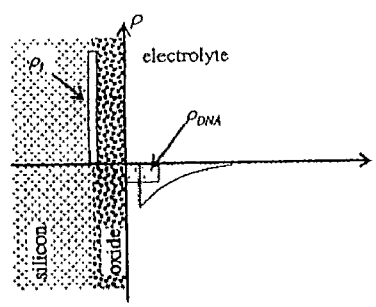
FIG. 11 schematically illustrates DNA adsorbed on the oxide-electrolyte interface. The length of 15-mer DNA is about 51 Å, while the thickness of the inner Helmholtz layer is typically about 5 Å. An appropriate electrolyte concentration is assumed to ensure that the diffuse layer is larger than the DNA.

In FIG. 11:

$\rho$: the vertical axis of the figure to describe the profile of the electrical charge density, arising from the immobilized DNA molecules and rearrangement of ions in the buffer solution $\rho_l$: the linear charge density induced in the carbon nanotube.

$\rho_{DNA}$: the volume charge density of the immobilized DNA, shown to span to a finite distance to the electrolyte in the realistic situation, instead of being collapsed to the interface and treated as a surface charge density in the simplified model.

Figure 12:
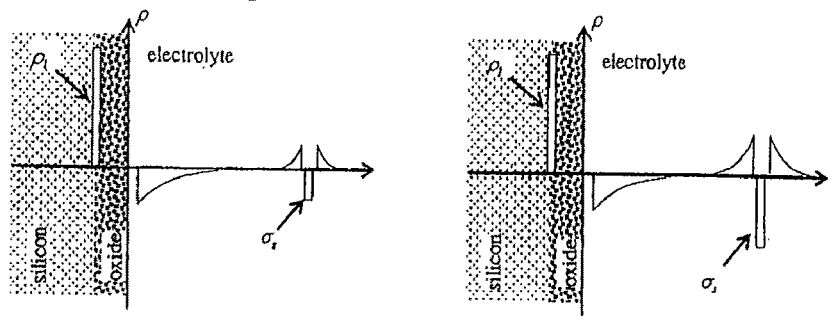
FIG. 12 illustrates the case where the charge to be detected is beyond the reach of the diffuse layers of the oxide-electrolyte interface.

In FIG. 12:

$\rho$: vertical axis of the figure to describe the profile of the electrical charge density; $\rho_{ion}$ volume charge density of negative ions in solution; $\rho_S$: volume charge density of the positive ions in solution which surrounds and screens $\sigma_s$; $\rho_l$: linear charge density induced in the carbon nanotube; $\sigma_s$: surface charge density of the immobilized molecule of interest. The figure demonstrates that the immobilized molecule must be situated close to the interface, otherwise its change will be screened by the surrounding ions in the electrolyte and cannot be detected by the device. Any change in the charge $\sigma_s$ will be screened by the surrounding diffuse layer and has effect to the transistor.

Figure 13:
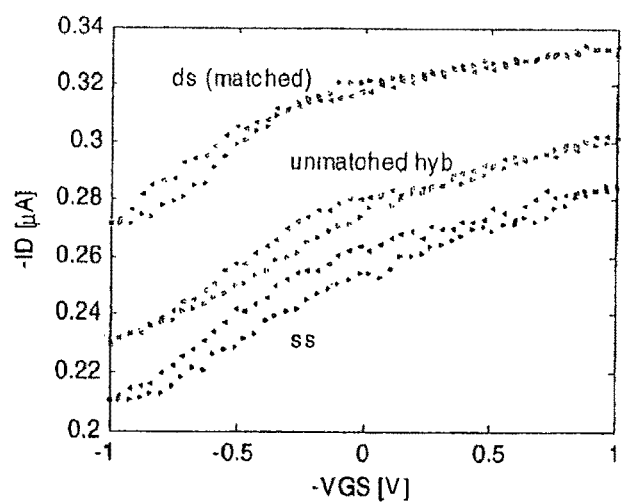
FIG. 13 illustrates transconductance curves of the carbon nanotube transistor (VDS=–0.1 v): (ss) after treated with single-strand DNA; (unmatched hyb) incubated with unmatched sequence of DNA; (ds matched) hybridized with complete matched DNA. Triangles denote sweep direction.
Figure 14:
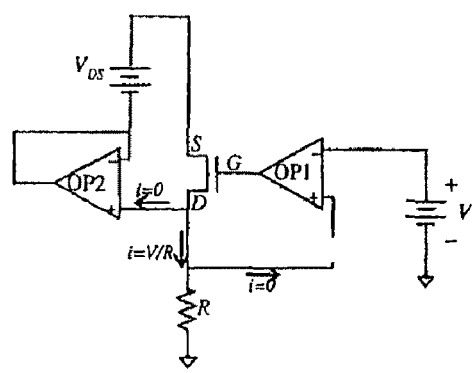
FIG. 14 illustrates a feedback circuit to fix $I_{DS}$ by adjusting voltage applied to the gate.

In FIG. 13:
ID: drain current;
VGS: voltage across source and gate;
ss: single stranded 15-base oligomer immobilized on the gate;
ds: double stranded DNA, achieved by exposing ss to its complementary oligomer and hybridized at room temperature;
unmatched hyb: ss exposed to non-complementary sequence and hybridized under same condition as in ds In FIG. 14:
V is voltage;
R is resistance;
S is source;
D is drain;
I is current;
$V_{os}$ is drain source voltage; and
G is gate.

Figure 15:
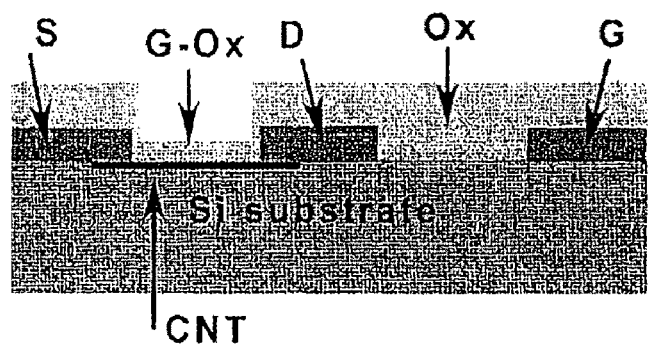
FIG. 15 is a cross-sectional view of a carbon nanotube transistor. A semiconducting carbon nanotube is contacted by two electrodes, labeled (S) and drain (D) on opposite ends, and covered with an insulting oxide barrier. The source and drain electrodes have electrical connections (not shown) to bring signals from outside of the oxide barrier.

In FIG. 15:
S is source;
D is drain;
G is gate;
$O_x$ is insulating oxide; and
G-$O_x$ is gate oxide.

Figure 16:
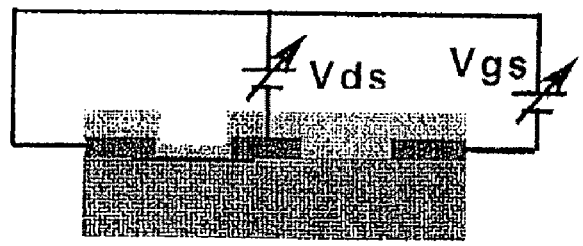
FIG. 16 illustrates voltage connections for transconductance measurements.
Figure 17:
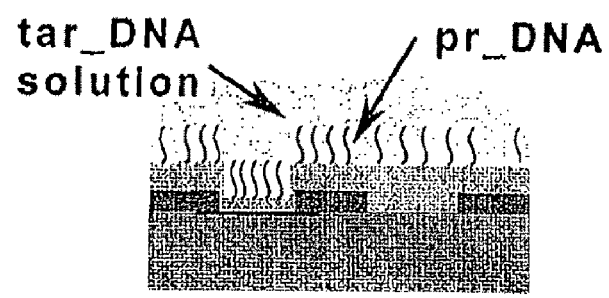
FIG. 17 a scheme for DNA-DNA hybridization. Functionalized probe DNAs (pr_DNA) are immobilized on the oxide surface using silane-acrydite binding. A solution containing non-modified target DNA (tar_DNA) is introduced for complementary hybridization.

In FIG. 16:
$V_{ds}$ is drain source voltage; and
$V_{gs}$ is gate source voltage.

THE APPARATUS OF THE PRESENT INVENTION

A. Overview of the Present Apparatus

Semiconducting carbon nanotubes function as channels in between two conductors and respond to a gating field by modulating the channel conductance. Carbon nanotubes are very sensitive charge detectors, and thus are conducive to achieving high sensitivity DNA detection, for example. The fabrication of a carbon nanotube transistor is easy, simple and well-adaptable to a flexible substrate. The cylindrical geometry of the nanotube allows for a less stringent requirement on gate oxide thickness. In accordance with the present invention, the nanotube is insulated with silicon oxide or nitride, for example, and probe material is immobilized on the insulating layer to avoid direct modification of the nanotube by the probe material or the electrolyte buffer.

In accordance with another aspect of the present invention, iron nanoparticles are used as a catalyst for effecting carbon nanotube growth. In particular, sub-monolayer thin iron films are deposited by thermal evaporation under less than $10^{-10}$ atm pressure. Upon exposure to ambient atmospheric pressure, nanoparticles of iron oxide are formed, and later reduced by high temperature exposure to hydrogen during carbon nanotube growth.

B. Carbon Nanotube Transistors

The present apparatus contains an array containing up to hundreds of thousands of carbon nanotube transistors, wire-bonded to a circuit board that is easily fitted to a platform that houses circuitry of switches that control the addressing signal to each transistor. Each transistor is spotted with distinct biological probe material, such as DNA, RNA, peptide or cell surface receptor domain, so the device mimics a microarray of such probe material, with an important exception, being among things, that the transistor reader is built in. For example, since the DNA backbone is negatively charged only if it is dissolved, the charge detection measurement is done with the device in contact with the DNA electrolyte solution. Thus, the device is well-insulated and encapsulated in a robust package to prevent shorting among the leads by the electrolyte solution.

Figure 2:
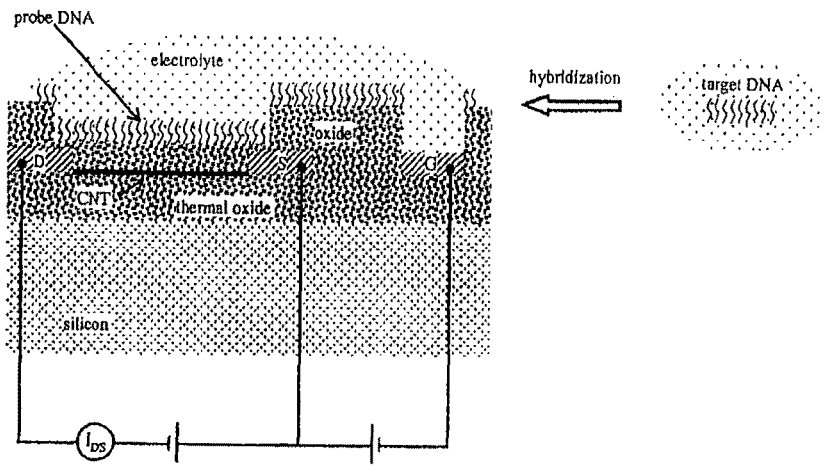
FIG. 2 is a schematic of a carbon nanotube transistor of the present invention for liquid gating. The drain source current ($I_{DS}$) is modulated by field effect from the DNA charges adsorbed on the oxide layer.

A schematic of a simple apparatus of the present invention is illustrated in FIG. 2 using DNA as a probe material. The drain (D), source (S) electrodes and the carbon nanotube channel bridging the two are insulated from the electrolyte solution by an oxide layer. Only the gate (G) electrode is in contact with the electrolyte solution. Probe DNA has been immobilized onto the oxide layer on top of the carbon nanotube channel. The apparatus does not need to be wet all the time. Only when charge measurement is performed does the DNA need to be dissolved. The channel conductance is a function of the field generated by the DNA charge adsorbed. As a prepared carbon nanotube usually exhibits p-type conduction, and DNA carries negative charges, the channel conductance increases upon hybridization which causes an increase in the number of charges adsorbed. If the drain-source potential is fixed, an increase in channel conductance is manifested as a drain-source current ($I_{DS}$) increase.

The present apparatus or device operates in a feedback mode to fix $I_{DS}$ by adjusting the gate-source potential ($V_{GS}$) upon hybridization. In this manner, the transistor action mechanism is decoupled from the electrostatics of the surface charge adsorption. The $V_{GS}$ shift reduces to a simple capacitance problem and is proportional to the change of number of charge adsorbed. Thus, the abundance of target DNA, for example, can be quantified by looking at the $V_{GS}$ shift which indicates the number of hybridization events. When it is desired to identify DNA, for example, the present apparatus can achieve the two functionalities of DNA microarray: (i) gene identification, by looking at which transistor in the array show channel conductance increase; and (ii) quantification, by looking at the amount of $V_{GS}$ shift.

C. Assembling the Present Apparatus

Carbon nanotubes (CNT) are grown on an insulating oxide substrate, such as a silicon oxide substrate using chemical vapor deposition (CVD). Generally, the substrate has several hundred nanometers (nm) thickness of thermal oxide on a p-type silicon substrate. Catalyst particles, such as iron particles, are deposited on the substrate either by iron nitrate dripping or brief evaporation of iron to generate iron dusting on the substrate. The growth is effected in a furnace at a temperature in excess of about 750° C., preferably about 900° C., with appropriate flow of methane, ethylene, hydrogen and argon gas. Carbon nanotubes grew out of the catalyst and form a mat on the substrate.

From the prepared CNT mat on the silicon dioxide or nitride substrate, the next step is to connect the nanotube channel to source and drain electrodes, by depositing gold film. The substrate is first spin-coated with photoresist, which is then patterned using contact photolithography. A chromium adhesion layer and gold layer are then deposited on the substrate by thermal evaporation; followed by lift-off to remove the gold layer on top of the photoresist. A typical source and drain separation or the channel length is about 5 µm. Unwanted nanotubes are etched out under oxygen plasma.

Figure 3:
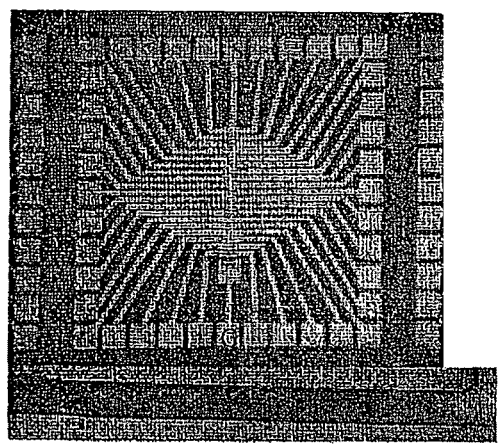
FIG. 3 is a photograph of a carbon nanotube transistor array of the present invention. Nanotubes bridge the gap between source and drain electrodes. (S) is the bonding pad for the common source electrode, and (G) is the bonding pad for the gate counter electrode. The square on the other end of (G) is in contact with the solution. Unmarked squares are bonding pads for drain electrodes. Shown are 38 transistors in a cell of 3 mm×3 mm.

FIG. 3 illustrates a transistor array of 38 transistors in one cell, and all have a common source for economizing space. Each electrode (drain or source) is connected to contact pad for wire bonding. In this case, the contact pad is 200×200 µm. The device is intended for liquid gating operation since the DNA should be dissolved in the buffer solution so there is also a common gate counter electrode for applying gate voltage.

To provide isolation to the nanotubes from the electrolyte buffer, a thin silicon oxide layer is evaporated on the device, followed by the thick plasma enhanced CVD (PECVD) of oxide layer (up to ~0.5 µm). The reasons for this redundancy is that the plasma process destroys the nanotube mat. The oxide layer at the active area is RIE (reactive ion etched) back again to get a thickness of ~100 nm, while leaving thick oxide on the other part.

Further, the present invention also provides a design and process for forming insulating gate material. The process entails depositing aluminum gate oxide by atomic vapor deposition. A thin layer of less than about 10 nm of silicon nitride is deposited on the top layer to improve the protection of the underlying carbon nanotubes from water. The resulting transistors have significantly improved conductance curves, i.e., less hysterisis, and better uniformity.

1. Design Parameters (a) Oxide Thickness

There are two contradicting requirements for the gate oxide thickness. On the one hand, a thick oxide is desired to minimize electrolyte current leakage, but on the other hand, a thin oxide is desired to maximize the gate coupling. The geometry of CNT reduces the requirement for extremely thin oxides. A nanotube buried under an oxide layer with surface charges on top of the oxide layer may be modeled by considering the capacitance between an infinitely long conducting cylinder and an infinite plane. Thus, can determine the appropriate oxide layer thickness by considering a standard textbook problem of an infinite cylinder and a grounded plane.

Figure 4:
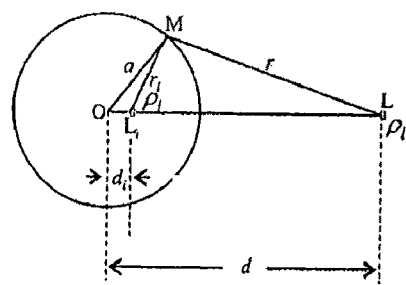
FIG. 4 illustrates the geometry for determining line charge next to a conducting cylinder.

The problem of the capacitance between an infinitely long conducting cylinder and an infinite plane is solved by the method of image. This is an extension of the problem of an infinitely long line charge ρi (C/m) located at a distance d from the axis of a parallel conducting cylinder of radius α. One locates an image line charge (ρi) that makes the cylinder surface an equipotential surface, and the dimensions in the problem is shown in FIG. 4.

Figure 5:
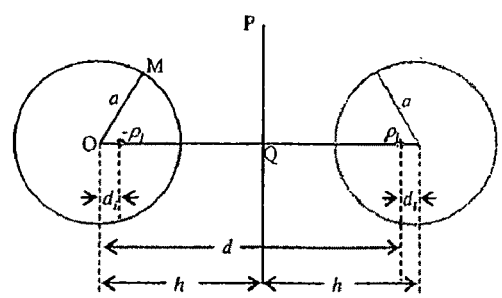
FIG. 5 illustrates the geometry for determining capacitance between a conducting cylinder and a plane.

Assigning $\rho i = d_i = a^2$ d makes the cylinder surface equipotential. To solve for the capacitance between a conducting cylinder and a plane, another cylinder is added as shown in FIG. 5. The original line change and the image line charge creates equipotential cylinders around each line charge, with the axes of the cylinders displaced by $d_i$ from the respective line charge. If the plane is inserted right at the center between the two line charges, it will be an equipotential plane, since each point on the plane is equidistant from both line charges.

The potential difference between the cylinder surface (M) and the plane (P) can be written as:

$$V_M - V_P = \frac{\rho_l}{2\pi\varepsilon} \ln \frac{a}{d}. \quad (1)$$

so that the capacitance per unit length is:

$$C = \frac{\rho_l}{V_P - V_M} = \frac{2\pi\varepsilon}{\ln(d/a)}.$$

But $$d = 2h - d_1 = 2h - a^2/d, \text{ or } d = h + \sqrt{h^2 - a^2}, \text{ so}$$

$$C = \frac{2\pi\varepsilon}{\ln\left(h/a + \sqrt{h^2 - a^2}/a\right)}.$$

We note that $\ln(x + \sqrt{x^2 - 1}) = \cosh^{-1} x$, so we can rewrite the capacitance as:

$$C = \frac{2\pi\varepsilon}{\cosh^{-1}(h/a)}.$$

This simple model suggests that the capacitance is a slow function of the oxide thickness (h), therefore, the requirement of fabricating very thin gate oxide to provide optimal gate coupling is largely alleviated. Thus, thick gate oxide may be used to avoid electrolyte current leakage without drastic losses in gate coupling. Typically, about 50 to 200 nm, preferably about 100 nm thick of oxide, is used on top of the drain source gap in between which carbon nanotube channels are bridging, and about 250-750 nm, and preferably about 500 nm, thick of oxide everywhere else.

(b) Contact Resistance

Figure 6:
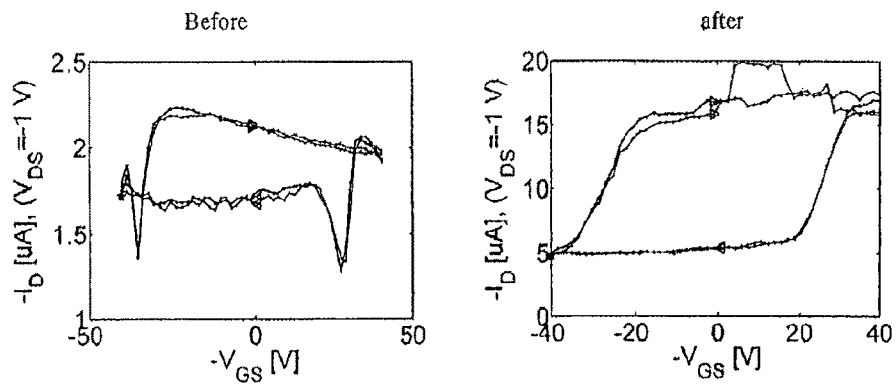
FIG. 6 shows that back gating I-V characteristics improve upon annealing: (left) before annealing, and (right) after annealing. Annealing temperature was 500° C. for one hour in vacuum.

While the carbon nanotube transistor mechanism of action remains under investigation, there are rationales and evidence therefor found in the literature suggesting $I_{DS}$ is controlled by the gate voltage through: (i) charges induced in the nanotube; (ii) modulation of Schottky barrier contact between the semiconducting nanotube and the metallic source and drain electrodes; or (iii) combination of both (i) and (ii). Unlike conventional MOSFET (metal-oxide-semiconductor field-effect transistor) where the source and drain are highly doped silicon, the material of drain source electrodes for the carbon nanotube transistor used in the present invention is gold, a different material from the nanotube channel. Contact resistances between drain and channel junction and between channel and source junction are therefore inevitable. In practice, regardless of the physical mechanism behind the transistor action, the preferred practice is to improve the performance by annealing. FIG. 6 shows improvement of contact resistance upon vacuum annealing of the device. The current level is higher for the same drain-source voltage and the curve shows less garble after annealing.

2. Device I-V Curve

Figure 7:
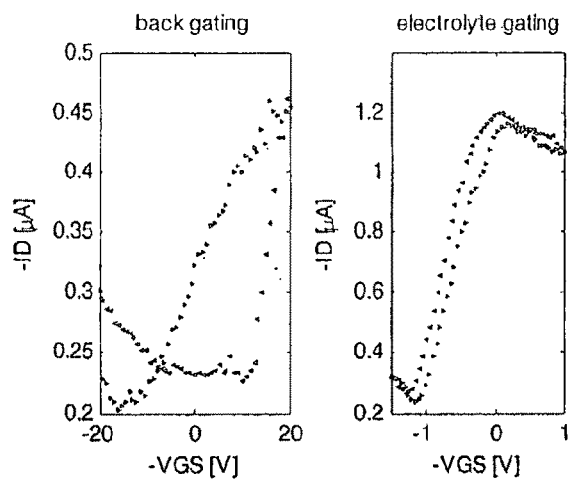
FIG. 7 illustrates a comparison of back-gating and electrolyte-gating on the same transistor. Triangles of the markers denote the gate voltage sweep direction (VDS=–0.1 v FIG. 8 illustrates the coupling mechanism of MPTMS to hydroxylated silicon oxide surface.

As depicted in FIG. 2, the apparatus in operation has to be in contact with the electrolyte solution. Gating is done through the electrolyte which is in contact with the gate electrode where $V_{GS}$ is applied. This is called electrolyte gating. However, there is also another way of gating, which we call back gating, i.e. through the back of the body of the silicon which is insulated from the nanotube channel by 300 nm thick of thermal oxide. FIG. 7 shows comparison between back-gating and electrolyte-gating to the same transistor. It is clear that electrolyte-gating requires less voltage range to sweep the transistor on and off, and the hysteresis effect is less prominent in the electrolyte-gating. The hysteresis is undesired but unavoidable and caused by trapped charges in the oxide layer that move around with the applied gate voltage. In practice, the apparatus is should initially biased towards one end to always choose the same hysteresis branch with sweeping in only one direction.

D. Probe Material Immobilization and Hybridization

1. Immobilization

Figure 8:
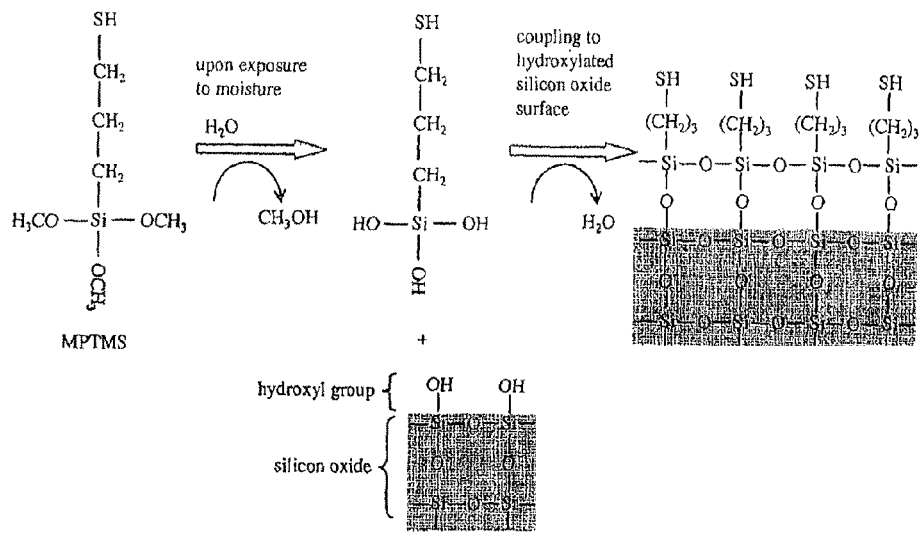

Probe material is immobilized on the insulating oxide or nitride surface through silane functionalization. The insulting oxide or nitride surface is exposed to brief oxygen plasma to generate hydroxyl groups on the surface, on which (3-mercaptopropyl)trimethoxysilane (MPTMS) can polymerize. The coupling of MPTMS to hydroxylated silicon oxide surface is shown in FIG. 8. Making aqueous solution of MPTMS substitutes the methoxy groups to hydroxyl groups. A water molecule is released during the coupling reaction, so it is important to perform the coupling in dry environment. But the polymerization of silane molecule with other silane molecules is inevitable, leading to formation of large globule of polymers that induce roughness and heterogeneity on the surface. After the surface is functionalized with mercaptan groups, the acrydite-modified probe oligonucleotides, for example, react readily with the mercaptan groups of the silane to form covalent bonds by overnight incubation of the probe oligonucleotides. We have used 15-mer oligonucleotide, for example. The surface is then treated with 100 mM of sodium acrylate for 15 minutes to passivate unbound MPTMS.

2. Hybridization

Hybridization with unlabeled or untagged target oligonucleotide is done under normal hybridization condition, i.e. 10 mM phosphate buffer solution pH 7, 0.3 M NaCl. Salt is very important to reduce electrostatic repulsion among two complementary strands to achieve hybridization. But, high salt or ionic concentration limits the apparatus sensitivity. Hence, repeated washing steps are necessary to reduce the salt without causing dehybridization. Washing is done at least three times with gradual decrease of salt concentration 0.3M, 0.1M, 10 mM, and finally the device is washed with 0.3M ammonium acetate pH 7, which is know to eliminate salt effectively. Electrolyte gating measurements are taken before and after hybridization and are always done under 1 mM phosphate buffer pH 7.

It has been suggested that target-DNA hybridization onto preimmobilizied probe-DNA on solid substrate follows the Langmuir adsorption model, which predicts that at high bulk concentration of the adsorbate, the surface will be fully covered by the adsorbate:

$$\frac{\Gamma}{\Gamma_{max}} = \frac{\beta C}{1+\beta C}$$

Where $\Gamma$ is the DNA surface coverage, $\Gamma_{max}$ is the maximum DNA surface coverage, C is the concentration of DNA in the bulk electrolyte, and $\beta$ is usually extracted from experiment and is typically in the range of $10^7$ $M^{-1}$ from fluorescence or surface plasmon resonance experiment.

E. Electrical Measurements

1. Device Electrostatic Model (a) Electrolyte Capacitance (Gudy-Chapman-Stern Model)

When an electrode carrying surface charges is immersed in an electrolyte solution, ionic space charges of opposite sign will build up in the electrolyte solution. Ions in the space charge cannot approach the electrode closer than the inner Helmholtz layer, thus they are called out Helmholtz layer or diffuse layer. Only chemically specific adsorbed molecules or ions can reside in the inner Helmholtz layer.

Ions can move around in the electrolyte. The flux of ions consists of diffusion of ions due to concentration gradient and drift of ions due to an electric field. One can imagine that ionic space charges build up close to the charged electrode, and decay with distance away from the electrode. In the case of thermal equilibrium where there is no net flux of ions in the solution, a potential difference is setup to semiconductor p-n junction.

Using the flux equation $j=DVc=qc\mu(-\Delta\phi)=0$, and Poisson equation $\partial^2\phi/\partial x^2=-\rho/\epsilon$, one can write down several important results in one dimensional case for 1:1 electrolyte (e.g. sodium chloride, which ionizes into the same amount of $Na^+$ and $Cl^-$ in the solution).

The relationship between the electric field and the potential at any arbitrary position in the electrolyte is:

$$\frac{\partial\phi}{\partial x} = -\sqrt{\frac{8k_BT c}{\varepsilon}}\sinh\left(\frac{\varepsilon\phi}{2k_BT}\right),$$

where the potential is set to zero at $x\to\infty$.

The above equation can be integrated to give:

$$\frac{2k_BT}{e}\ln\left(\frac{\tanh(e\phi(x)/4k_BT)}{\tanh(c\phi_0/4k_BT)}\right) = -\left(\frac{8k_BT c}{\varepsilon}\right)^{1/2}x,$$

where the potential is set at $x\to\infty$.

The above equation can be integrated to give:

$$\frac{2k_BT}{e}\ln\left(\frac{\tanh(e\phi(x)/4k_BT)}{\tanh(c\phi_0/4k_BT)}\right) = -\left(\frac{8k_BT c}{\varepsilon}\right)^{1/2}x,$$

where $\phi_0$ is the potential at $x=0$.

For small argument of hyperbolic tangent, it can be approximated as $\tanh(x)\approx x$. We Let $x=e\sqrt{2c/k_BT\varepsilon}$, then $\phi(x)=\phi_0\exp(-xx)$. Since $\phi_0$ is the potential at $x=0$, and the potential at $x=\infty$ is taken to be zero, than $\phi_0$ is the potential drop across the electrolyte.

According to the Stern model, ions cannot go arbitrarily close to the electrode. The ions have a finite size, they are probably solvated, or a layer of solvent might separate the ions from the electrode surface. Imagine that the ions can only go as close as $\delta$ to the electrode surface. In order to determine the relation of the potential drop across the electrolyte and the surface charge on the electrode surface, from Gauss' law, we can write:

$$\sigma_s = \varepsilon E(x=0) = -\varepsilon\left(\frac{\partial\phi}{\partial x}\right)_{\varepsilon=0}.$$

And since there is no charge in between $x=0$ and $x=\delta$, then $$\left(\frac{\partial\phi}{\partial x}\right)_{\varepsilon=0} = \left(\frac{\partial\phi}{\partial x}\right)_{\varepsilon=0} = \frac{\phi(\delta)-\phi_0}{\delta}.$$

Then, $$\left(\frac{\partial\phi}{\partial x}\right)_{\varepsilon=0} = -\sqrt{\frac{8k_BT c}{\varepsilon}}\sinh\left(\frac{\varepsilon\phi(\delta)}{2k_BT}\right)$$

$$-\frac{\sigma_s}{\varepsilon} = -\sqrt{\frac{8k_BT c}{\varepsilon}}\sinh\left(\frac{e}{2k_BT}(\phi_0-\sigma_s\delta/\varepsilon)\right)$$

And finally, the potential drop across the electrolyte is $$\phi_0 = \frac{2k_BT}{e}\sinh^{-1}\left(\frac{\sigma_s}{\sqrt{8k_BT c\varepsilon}}\right)+\frac{\sigma_s\delta}{\varepsilon}. \quad (2)$$

The voltage drop derived in this section is based on thermal equilibrium assumption, which is attainable when good insulation between the nanotubes and the electrolyte exists. Leakage current is ignored in this analysis, however electrolyte leakage current is undesirable, because it means that the electrodes have degraded by Faraday process.

An applied voltage between the source and the gate counter electrode is the sum of potential drop across the nanotube channel, the oxide layer, the oxide-electrolyte interface, and the electrolyte-gate counter electrode interface, or $V_{app} = \varnothing_{transistor} + \varnothing_{ox} + \varnothing_1 + \varnothing_2$. Thermal equilibrium is assumed where there is no net ionic flux in the electrolyte. The change of the potential drop across the nanotube channel can be estimated.

The voltage drop between the electrolyte and the gate counter electrode from Guoy-Chapman-Stern model derived in the preceding section is given by:

$$\phi_2 = \frac{2k_B T}{e} \sinh^{-1}\left(\frac{\sigma_2}{\sqrt{8k_B T \varepsilon}}\right) + \frac{\sigma_2 \delta}{\varepsilon},$$

where now $\sigma_2$ is the surface charge density on the counter electrode. This potential drop is expected to be about the same before and after DNA hybridization, for example, because the surface charge density depends on the conditions of the electrolyte and the counter electrode, which are not changed upon hybridization.

Now looking at the inner Helmholtz layer, to which probe DNA is attached, for example, Gauss' law is applied at the interface:

$$\varepsilon_{cu}(-E_{cu}) + \varepsilon_{liq} E(x=\delta') = \sigma_s.$$

where $\sigma_s$ is the surface charge density of the immobilized DNA, which will increase and at most double upon hybridization. $\delta$ is in the order of several Angstrom and denotes the boundary of inner and outer Helmholtz layers.

The voltage drop across the oxide and electrolyte interface is then:

$$\phi_1 = \frac{2k_B T}{\varepsilon} \sinh^{-1}\left[\left(\frac{\varepsilon_{be}}{8k_B T_C}\right)^{1/2} E(x-\delta^*)\right] + E(x=\delta^*) \cdot \delta$$

$$\phi_1 = \frac{2k_B T}{e} \sinh^{-1}\left[\frac{\sigma_s + \varepsilon_{cf} E_{as}}{(8k_B T_C \varepsilon_{liq})^{1/2}}\right] + \frac{\sigma_s + \varepsilon_{mr} E_{ox}}{\varepsilon_{liq}} \delta.$$

We can estimate $E_{oz}$ by the electric field at the point $Q$ in Fig. 5:

$$E_{ca} = \frac{2\rho_l}{2\pi\varepsilon_{ax}} \frac{1}{(h-d_l)}, \quad d_l = a^2 / \left(h + \sqrt{h^2 - a^2}\right).$$

The voltage drop across the oxide layer is given by:

$$\phi_{oz} = \frac{\rho_j \cosh^{-1}(h/a)}{2\pi\varepsilon_{oz}}.$$

Summing up all the voltage drop terms:

$$V_{app} = \phi_{transistor} + \phi_{oz} + \phi_1 + \phi_2. \quad (3)$$

(b) Voltage Shift as a Function of Adsorbed Charge

It is assumed that the apparatus is operating in a feedback mode to keep $I_{DS}$ constant, so that electrostatics of the adsorbed charges can be decoupled from the carbon nanotube transistor action mechanism.

By fixing IDS, is fixed; therefore $\varnothing_{transistor}$ and $\varnothing_{ox}$ are also fixed. The feedback circuit only needs to compensate for the change of $\varnothing_1$ due to hybridization. Plugging in typical numbers: h=100 nm, a=2 nm, $\epsilon_{ox}$=3.9 $\epsilon$0, $\epsilon_{liq}$=80 $\epsilon_0$ T=300 K, and $\delta$=5 Å, can write:

$$\phi_k[\text{volt}] = 0.051 \sinh^{-1}\left[\frac{\sigma_s[\text{coul/m}^2] + 1.5 \times 10^{-4}\phi_{cr}[\text{volt}]}{0.12\sqrt{c[\text{mol/liter}]}}\right] + \quad (4)$$

$$0.7(\sigma_s[\text{coul/m}^2] + 1.5 \times 10^{-4}\phi_{oz}[\text{volt}])$$

Typically all voltages involved are in the order of one or two volts. If the ionic strength of the electrolyte is c=1 mM, then the denominator inside the bracket of sin h$^{-1}$ is 3.79×10$^{-3}$, so the first term is the dominant term.

Probe material, such as DNA, cannot reside completely within the inner Helmholtz layer. Typically the inner Helmholtz layer is in the order of $\delta$=5 Å thick, but the length of 15-mer DNA is 51 Å. The more realistic picture of the interface should look more like the one in FIG. 11. The free ion concentration is Boltzmann-distributed in energy. We can write down the Poisson's equation as:

$$\frac{\partial^2 \phi}{\partial x^2} = \sum_i -\frac{q_1 c_2(\infty)}{\varepsilon} \exp\left(-\frac{q_1 \phi(x)}{k_B T}\right) - \frac{-|\rho_{DNA}|}{\varepsilon}$$

$$\frac{\partial^2 \phi}{\partial x^2} = \frac{\varepsilon c}{E} \exp\left(-\frac{\varepsilon\phi(x)}{k_B T}\right) - \frac{-ec}{\varepsilon} \exp\left(\frac{e\phi(x)}{k_B T}\right) - \frac{-|\rho_{DNA}|}{\varepsilon}$$

$$= \frac{e}{\varepsilon}\sinh\left(\frac{\varepsilon\phi(x)}{k_B T}\right) + \frac{|\rho_{DNA}|}{\varepsilon}$$

Unfortunately, the above equation cannot be solved for a closed form expression. Typically two extreme cases are solved in the textbook: (i) quasi-neutrality approximation, and (ii) depletion approximation.

In quasi-neutrality approximation, $\partial^2\varnothing/\partial x^2$ is assumed to be very small, or the charge is nearly neutral. The positive ions compensate for the negative DNA charges:

$$c \exp(-e\phi/k_a T) \times |\rho_{DNA}|$$

$$\phi \approx k_B T/e \cdot \ln(|\rho_{DNA}|/c)$$

Or $\phi \propto \ln(|\rho_{DNA}|) \quad (5)$

In the other extreme approximation, the depletion approximation, where the free ions are depleted and cannot compensate for the DNA charges, we can write:

$$\frac{\partial^2 \phi}{\partial x^2} = \frac{|\rho_{DNA}|}{\varepsilon}$$

$$\frac{\partial \phi}{\partial x} = \frac{|\rho_{DNA}|}{\varepsilon} + \text{constant}.$$

(c) Device Sensitivity

Simple calculations can be performed to project the minimum concentration of the 15-mer target DNA needed to induce appreciable voltage shift. Let us assume we can detect a change of 51 mV, which is the prefactor of the sin h$^{-1}$ term. It is a safe assumption indeed, because 51 mV is 2 k8 T/e. The denominator inside the sin h$^{-1}$ bracket is 3.79×10$^{-3}$, for c=1 mM. If the change is $\sigma_s$ is equal to 3.79×10$^{-3}$, then the $\varnothing_{ox}$ term can be neglected, and the $\varnothing_1$ change is approximately 51 mV.

To achieve 51 mV in the $\varnothing_1$ change, we need a surface coverage change of 3.79×10$^{-3}$ coul/m$^2$. For 15-mer oligonucleotide, we assume that each base carries one electron charge in solution, so each molecule carries 15×1.6×10$^{-19}$ coul. The surface coverage needed is then 1.57×10$^{15}$ molecule/m². This surface concentration imposes the requirement for the minimum surface density of probe-DNA immobilization. That is, if the probe DNA is not dense enough, the change in surface charge upon hybridization to target DNA cannot yield the desired voltage change. The maximum DNA surface coverage is achieved when all of the DNA strands fill up the surface in upright strand orientation. Assuming the strand radius is 6 Å gives:

$\Gamma_{max} = (\pi r^2)^{-1} = 8.8 \times 10^{17}$ molecule/m².

Using the Langmuir adsorption model, and β value of $10^7$ M$^{-1}$, we obtain that the target concentration in the bulk needed to achieve the desired voltage change is ~20 nM.

Although the sensitivity predicted by the model is only in the order of 20 nM, but it has been shown experimentally that sensitivity down to fM is achievable with field effect detection. This suggests that the assumption of β may actually underestimate the sensitivity. We project that our approach can also achieve fM sensitivity.

But the electric field $$\frac{\partial \phi}{\partial x} = \frac{|\rho_{DNA}|}{\varepsilon} x - E_0$$

$$\phi(x) = \frac{|\rho_{DNA}| x^2}{2\varepsilon} - E_0 x + \phi_l$$

The potential drop across the length (l) of the DNA, is $\phi_D - \phi(x) = E_0 l - |\rho_{DNA}| l^2 / 2\varepsilon$ Or $\phi \propto |\rho_{DNA}|$ (6)

The quasi neutrality approximation predicts that the potential drop is proportional to the logarithm of the DNA charges, while the depletion approximation predicts that the potential drop is linearly proportional to the DNA charges. The realistic case may lie in between the two approximations. This is actually consistent with the behavior of the sin h$^{-1}$ function previously derived from the potential drop, because sin h$^{-1}$(x)≈x for small x, and sin h$^{-1}$(x)≈ln(2x) for large x.

FIG. 12 illustrates a situation where the charge to be detected is beyond reach of the diffuse layer of the oxide-electrolyte interface. Any change in the charge $\sigma_s$ will be screened by the surrounding diffuse layer and has no effect on the transistor.

Low ionic salt concentration is used in the electrolyte solution during the measurement, to ensure that the field from the charge to be detected can reach the carbon nanotube channel. Consider in FIG. 12, where the charge to be detected is farther than the Debye length. The increase in $\sigma_s$ has no effect on the transistor because it only modulates the diffuse layer around it, and the transistor does not feel any electric field from $\sigma_s$ since the field has been screened by the diffuse layer. So it is very important that the diffuse layer of the oxide-electrolyte interface overlaps with the charged biomolecules. The requirement that $\kappa^{-1}$ has to be large imparts limitation to the ionic strength (c) of the electrolyte, since $\kappa^{-1} = 1/e \cdot \sqrt{k_B T \varepsilon / 2c}$ is inversely proportional to square root of c. If we take for example a 15-mer oligonucleotide and the length of one monomer is 3.4 Å, then k$^{-1}$>51 Å, or c<3.6 mM.

$\kappa^{-1} = 1/e \cdot \sqrt{k_B T \varepsilon / 2c}$

2. Change of I-V Curve Upon Hybridization: Preliminary Proof of Principle

FIG. 13 shows the transconductance curve of single strand DNA, unmatched hybridization, and double strand DNA after completely matched hybridization. As prepared, carbon nanotube transistors generally show p-type conduction. Negative charges from DNA adsorbed on the gate serve as extra negative bias voltage applied that would increase the conductance of nanotube channel. It is clear that the current level was boosted after the matched hybridisation due to the increase number of charged adsorbed. A slight increase in current is still observed after unmatched hybridization due to non-specific binding. All of the three transconductance curves were measured from the same transistor and taken sequentially from single strand (ss): 5'/Acrydite//Spacer18/ATC CTT ATC AAT ATT -3' (SEQ ID NO:1), hybridization with unmatched sequence: 5'/ATC CTT ATC AAT ATT -3' (SEQ ID NO:1) (unmatched hyb), and hybridization with matched sequence: 5'/AAT ATT GAT AAG GAT -3' (SEQ ID NO:2) (ds matched).

FIG. 13 illustrates transconductance curves of the carbon nanotube transistor (VDS=-0.1V): (ss) after treated with single-strand DNA; (unmatched hyb) incubated with unmatched sequence of DNA; (ds matched) hybridized with complete matched DNA.

Triangles denote sweep direction.

F. Summary of the Technique for Microarray Application

The aforementioned discussion relates the expected change in the gate voltage as a function of the amount of charge deposited on the gate. From a device perspective, one can approximate the behavior of the CNT transistor as a PMOS operating under the so-called triode region. Under this assumption, the drain current is modeled as:

$$i_d = K[2(v_{gs} - v_t) v_{ds} - v_{ds}^2)], \quad (7)$$

where K is a parameter that determines the sensitivity, vt is the effective threshold voltage, vds is the applied potential between drain and source, and vgs is the applied potential between the gate and source. K and vt are intrinsic properties specific to each transistor and may vary from transistor to transistor. In the presence of hybridization, the net effect is the change in the threshold voltage $v_t$ which will be compensated by a corresponding change in $v_{gs}$ $$\delta i_d = \frac{\partial i_d}{\partial v_{gs}} \delta v_{gs} + \frac{\partial i_d}{\partial v_l} \delta v_{gs} = 2K v_{ds} \delta v_{gs} - 2K v_{ds} \delta v_l. \quad (8)$$

If we employ a feedback circuit such that the current is kept constant, then we can (7) to zero to obtain. In other words, the change in $v_{gs}$ is equal to, $$\delta v_{gs} = \delta v_t \quad (9)$$

This relationship is independent of the transistor property. Furthermore, the change in vgs can be used as a direct measure of the charge of the bound DNA molecules given by equations (5) and (6) for quasineutral or depletion approximations respectively. Thus, the measurement of the change in gate voltage after hybridization can provide a means to directly quantify the amount of bound charge. This approach is a fundamental enabler for gene expression experiments without the need for labeling.

The general methodology for microarray use as follows. A chip containing an array of carbon nanotube transistors is fabricated on a suitable substrate. The drain, source and gate electrodes are exposed for electrical contact, and an external multiplexing circuit is developed for each transistor. A microfluidic channel made of PDMS or suitable polymer is fabricated on the chip surface to direct the flow of probe and target oligonucleotide, such as DNA, solutions. Prior to DNA exposure, a preliminary scan of the transconductance curves will be measured for each transistor and will serve to identify working transistors as well as establish the baseline characteristics. Next, specific DNA solutions with complementary sequences to the target genes and with appropriate terminal modification for substrate binding are immobilized on the transistors. An automated spotter immobilizes different oligonucleotide sequences throughout the array in complete analogy with existing fluorescent-based microarrays. Hybridization is then performed on a target solution, and the voltage shift at constant current will be measured for each transistor using appropriate protocols. The operating point of the current is set at the steepest point of the transconductance curve to simultaneously increase the sensitivity and decrease the data acquisition time. In order to implement the equivalent of competitive gene expression experiments a second chip is fabricated and the same complementary DNA solutions, for example, are immobilized on the second chip. Hybridization and measurements of the voltage shifts are conducted as in the previous case, except that the target solution is prepared using the second sample. The concentration normalization chips corresponding to DNA sequences that are known to be conserved in both samples.

G. Testing Sensitivity of the Apparatus from Transistor Characteristics

Figure 21:
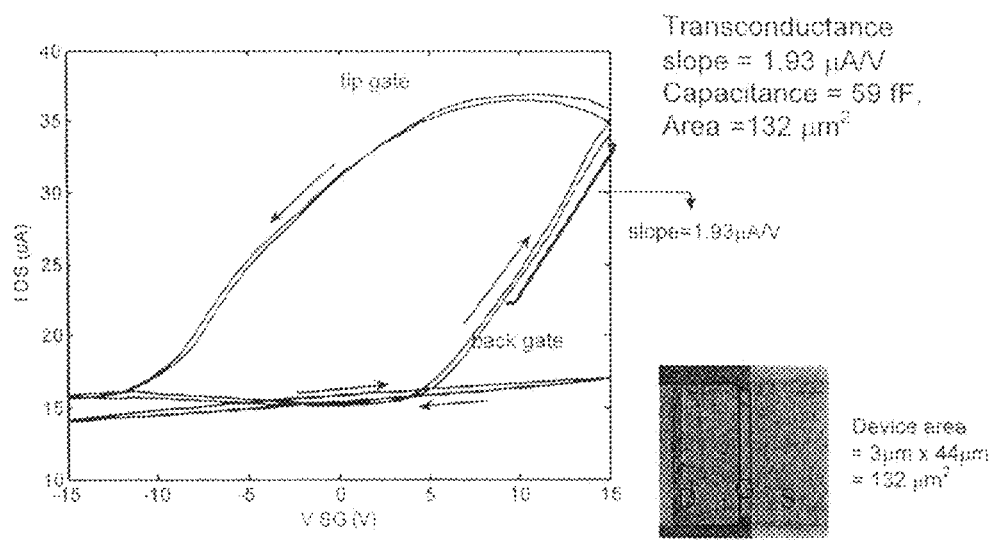
FIG. 21 illustrates sensitivity testing whereby sensitivity of the apparatus is estimated from the transistor characteristics.
Figure 22:
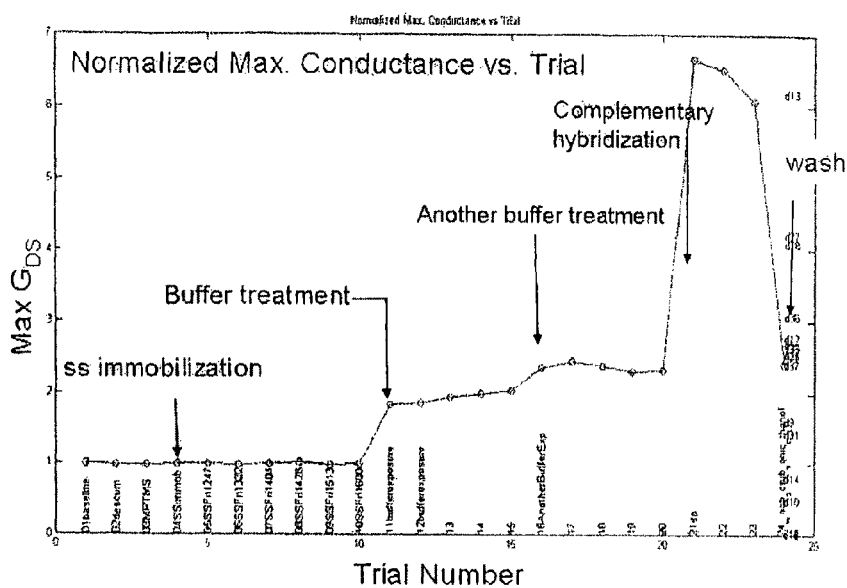
FIG. 22 illustrates response with various buffers and treatments. Increase in conductance is observed as a function of treatment. The largest change in conductance is due to complementary binding which increased conductance from 2 to 6.5. Subsequent washing and denaturization reduced conductance significantly.
Figure 23:
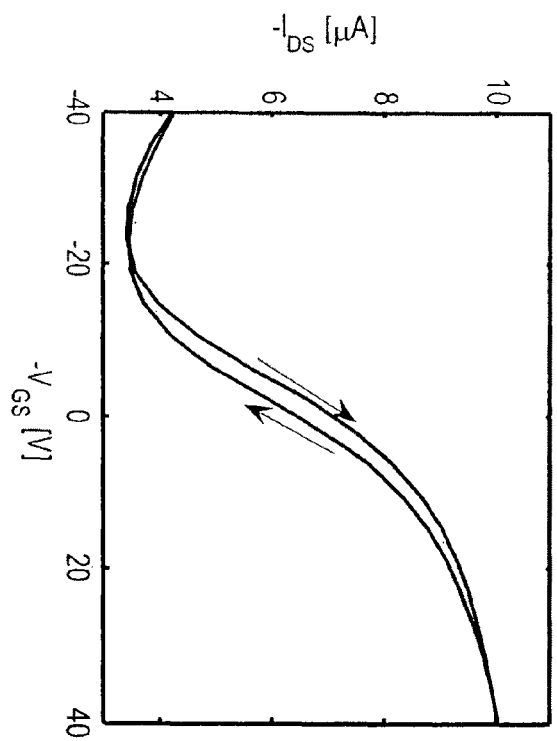
FIG. 23 illustrates characteristics of a transistor fabricated using aluminum oxide as a gate material. Significantly improved performance was noted.

Referring to FIG. 21, the following procedure is used to test the sensitivity of the present apparatus from transistor characteristics.

Transconductance slope=1.93 µA/V
Capacitance=59 fF, area=132 µm$^2$
To induce 1V of VGS change we need a surface charge density of:

$$\frac{1V \times 59\, fF / (15\, \text{bases} \times 1.6 \times 10^{-19}\, Coul)}{132 \times 10^{-5}\, cm^2} = 18.6 \times 10^9\, \text{molecules/cm}^2$$

Using Langmuir adsorption model to relate surface density to volume density:

$$\frac{\Gamma}{\Gamma_{max}} = \frac{K_A C}{1 + K_A C}$$

$\Gamma_{max}$ (maximum surface coverage) is obtained by assuming the DNA to be a rod like structure with a base of 6 Å radius and a height of 3.4 Å per base. Then $\Gamma_{max} \approx 9 \times 10^{13}$ molecules/cm$^2$, if all DNA stand upright, or $\Gamma_{max} \approx 3 \times 10^{13}$ molecules/cm$^2$ if all 15-mer DNA lie down horizontally. Typical $K_A$ is $6 \times 10^7$ M$^{-1}$.

Assuming worst case scenario, that all DNA lie down, we use $\Gamma_{max} \approx 3 \times 10^{13}$ molecules/cm$^2$. The needed volume concentration to achieve $\Gamma = 3 \times 18.6 \times 10^9$ molecules/cm2 in order to induce 3 V change or $3 \times 1.93$ µA increase in drain source current is: $\approx 31$ pM.

H. Various Uses of the Present Apparatus

Figure 18:
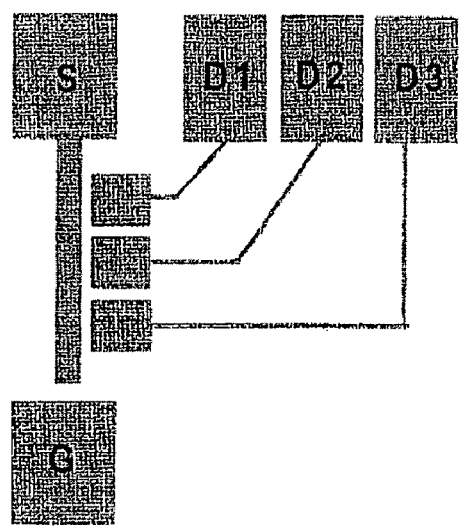
FIG. 18 illustrates a single well transistor setup for a single oligomer sequence, which contains a redundant set of drain and CNT connections.
Figure 19:
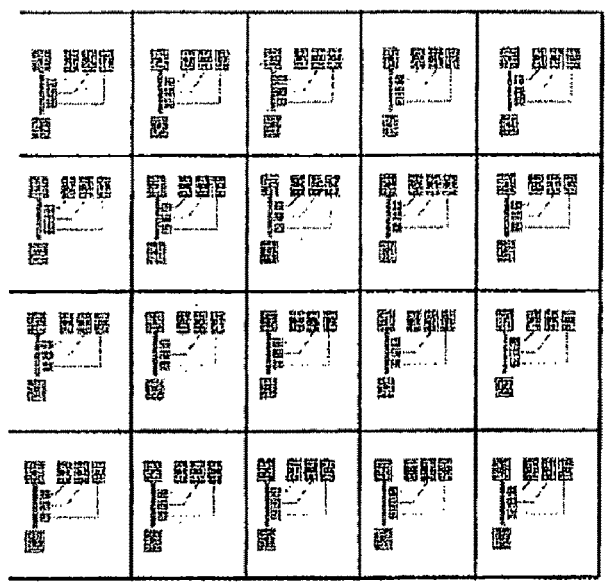
FIG. 19 illustrates an array of transistor wells for implementing hybridization experiments for multiple target sequences.
Figure 20:
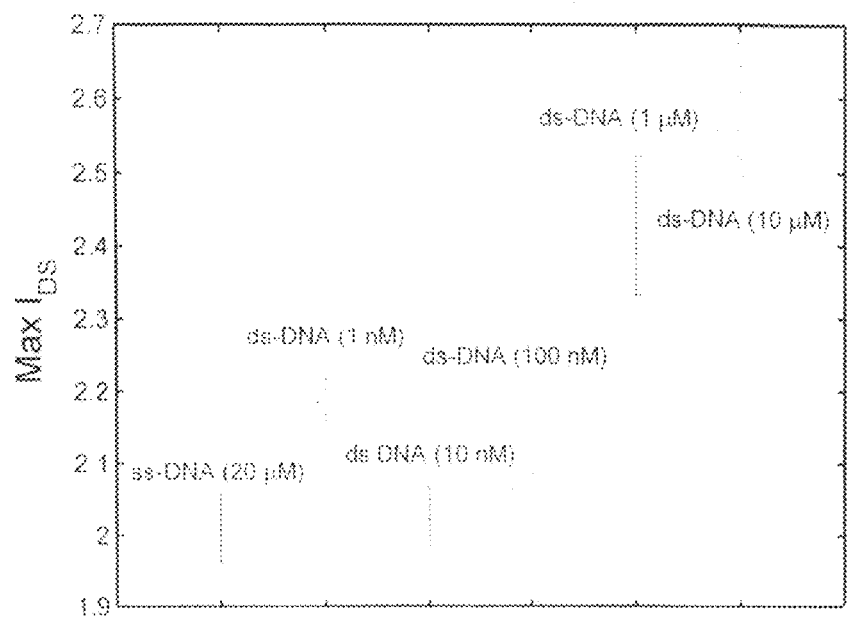
FIG. 20 illustrates a plot of maximum current versus concentration for a single transistor sensor. 20 μM probe DNA was used. Monotonic increase of sensor current from 100 nM and higher. A nitride-gated transistor was used.

The present apparatus may be used in a large variety of fields and to accomplish diverse objectives. For example, the apparatus may be used as a point-of-care clinical tool to examine certain forms of cancer wherein the knowledge of the expression of certain genes in the mRNA and miRNA can provide the basis for diagnosis, prognosis and potential treatment. More significantly, the invention is potentially applicable towards the sensing of a plethora of biological materials such as certain proteins, metabolic by products, drugs and even whole cells. The system is sufficiently adaptable to incorporate artificial nucleic acids, commonly referred to as aptamers, that are sensitive to the aforementioned biological materials. Thus, in general the invention can be used in the following areas:

Medical diagnosis and Preventive screening,
Drug discovery
Genetics and genetic screening
Bioagent detection for Homeland Security & Fighting Forces
Forensics and law enforcement Although the apparatus of the present invention may be constructed with one chip having from one to up to about 100 CNTs, the inclusion of a plurality of chips in an apparatus is explicitly contemplated. For example, apparatii having several, dozens, hundred or thousands of chips are contemplated. See FIGS. 18 and 19, for single chip and multiple chip arrays, respectively.

For example, it is explicitly contemplated to provide 600-700 chips in an array with from about 25 to 50 CNTs per chip, whereby each CNT is spotted with a single human gene. Thereby, genes of the known human genome may be accommodated in order to detect mutations. This includes genes presently know as well as those yet to be defined.

Further, it is explicitly contemplated to use cell receptor surface sequences as probes for viruses. It is well known, for example, that viral envelope glycoproteins bind to certain cell surface receptors.

Thus, in accordance with the present invention, any biological probe material may be used in the microarray to detect target material or materials in a sample. For example, nucleotide probes may be used which are complementary to characteristic pathogen products. See U.S. Pat. No. 4,358,535, which is incorporated herein by reference in the entirety. As another example, probes may be used having cell surface receptor domains. See U.S. Pat. Nos. 5,861,479; 6,093,547 and 6,905,685, all of which are incorporated herein by reference in the entirety. Moreover, aptamer probes may be used for detection of various drugs. See U.S. Pat. No. 5,789,163, which is incorporated herein reference in the entirety.

Additionally, as noted above, any conventional method of chip printing or spotting may be used to prepare the microarrays of the present invention: See U.S. Pat. Nos. 5,556,752; 6,953,551; 6,656,725; 6,544,698 and 6,594,432, all of which are incorporated herein by reference in the entirety.

Reference will now be made to certain Examples which are provided solely for purposes of illustration and which are not intended to be limitative.

EXAMPLE 1

Use of Catalysts in Forming CNTs

Figure 24:
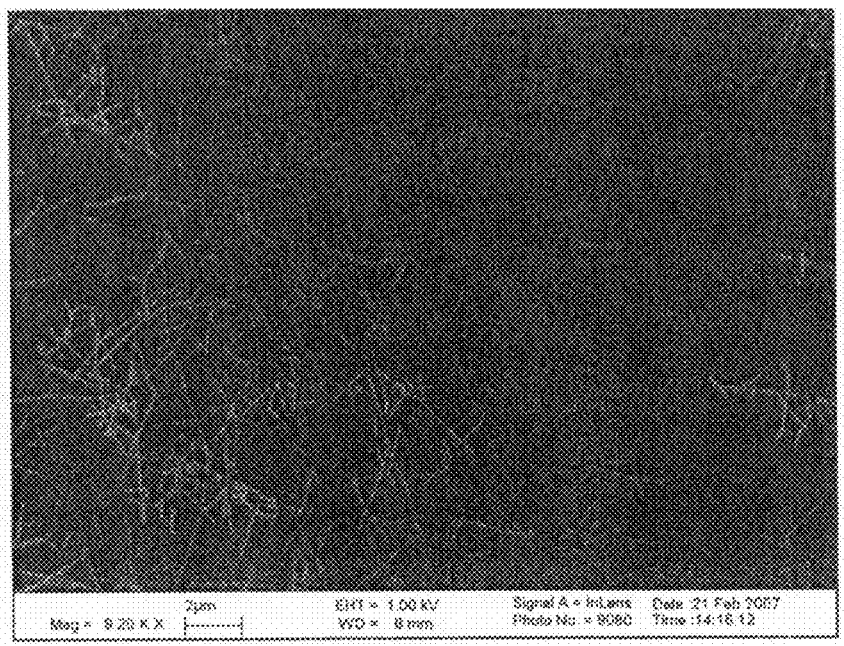
FIG. 24 show CNTs grown from Fe catalysts prepared by depositing a very thin layer (less than 1 nm) of Fe film by using ultra high vacuum iron deposition techniques.
Figure 25:
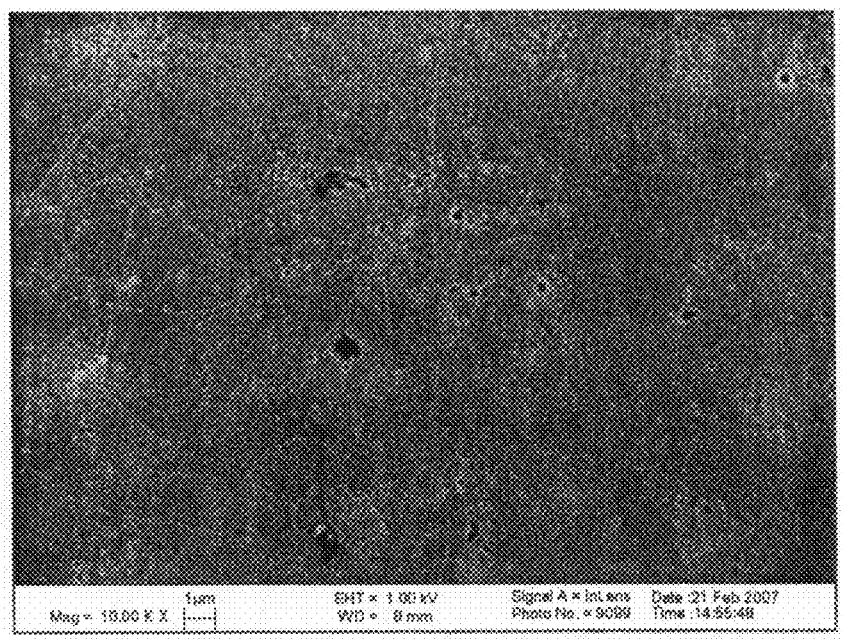
FIG. 25 shows CNTs grown out of Fe Pt particles prepared using cluster fabrication technique.

At least two methods may be employed for creating Fe nanoparticles that act as catalysts for CNT growth: a). Ultra high vacuum deposition of Fe at a thickness of less than 0.5 nanometers; and b). Formation of FePt particles using "nanocluster gun" technique of Ping Wang at Univ. of Minnesota. FIGS. 24 and 25 show the growth of CNT for each catalyst. Both produce CNTs, but longer and sparsely distributed CNT's are formed on FePT clusters. Any conventional method for forming CNTs may then be used with the Fe-containing catalysts.

EXAMPLE 2

Gold Deposition to Connect NT Channel to S and D Electrodes

Gold contracts are made using standards contact photolithography techniques and depositing gold to the defined area using physical vapor deposition technique. Briefly, standard contact photolithography involves coating the substrate/sample with a light-sensitive material, or a photoresist, which dissolves or hardens depending on the type upon exposure to light and subsequent developer solution. Patterns from a pre-drawn mask are transferred to the photoresist by exposing it to an ultraviolet light through the mask. A physical vapor deposition technique involves vaporizing solid material of interest, which is gold for this particular purpose, through various methods such as: resistive heating, electron beam heating, plasma sputtering, such that the vapor condenses on the substrate/sample thereby creating a thin film on the substrate/sample. Gold adhesion towards the oxide substrate/sample is improved by first depositing a thin coating of chromium or titanium to act as the wetting layer.

EXAMPLE 3

Preparation of Aluminum Oxide Gate Material

A preferred method for creating oxides, such as aluminum or hafnium oxides is by atomic layer deposition. Atomic layer deposition (ALD) is a known deposition method in which a film is built up one atomic layer at a time by saturating the functional group of the surface with a suitable precursor. The ALD cycle/steps to deposit aluminum oxide starts by saturating the surface, which inevitably contains hydroxyl group due to air moisture, with trimethyl aluminum (TMA). After excess/unreacted trimethyl aluminum is removed, water vapor is introduced to convert the methyl group of TMA to hydroxyl group, releasing methane as the byproduct. The newly converted hydroxyl group is now ready to react with another cycle of TMA exposure. Cycles of introduction of TMA and water vapor are repeated until the desired thickness is achieved.

EXAMPLE 4

Probe Attachment to the Insulating Oxide Layer

DNA probes are attached to the insulating oxide layer by a strong covalent bond between attachment molecule. There are a number of protocols and chemistry employed for this process. In one approach, an Acrydite™ molecule is added to the probe DNA sequence by linking it to the 5' terminal of each DNA during DNA synthesis. In other preparations, a spacer molecule such as a chain or carbon is included between the probe DNA and Acrydite. Concurrent with DNA synthesis, the oxide surface is functionalized with a thiol (sulfur) group of 3-mercaptopropyltrimethoxysilane (MPTMS). Functionalization of MPTMS to the insulating oxide layer is done in vapor phase, where a small volume of MPTMS solution (~0.1 mL) is placed at the bottom of glass container and the sample to be functionalized is mounted faced down at the top of the glass container. The bottom of the container is then heated (~60° C.) to drive the MPTMS vapor towards the sample for about 10 minutes. Excess/unreacted chemicals from the sample are driven off by means of thermal gradients, i.e., the bottom part of the container is cooled while the top part is heated. DNA probe attachment is done by pipetting and incubating the solution of the probe of interest which contains the attachment molecule to the MPTMS functionalized oxide layer. The chemical constitutes are shown below.

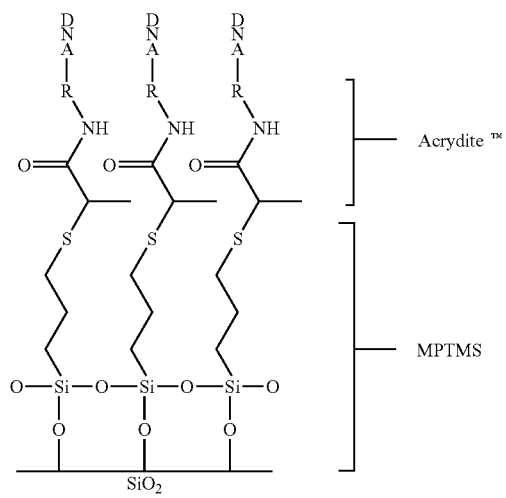

Since the chemical attachment is dependent upon the substrate surface, other methods, such as the functionalized of the surface with amine groups may also be used.

EXAMPLE 5

Exemplary Circuitry Means for Detecting Change in Charge and on Automated Sensing System The electric charge of the biomolecule is detected as an apparent threshold voltage shift in the sensor. An increase in the negative charge of DNA hybridizing, for example, near the electrolyte-oxide interface will cause a decrease in drain current of an n-channel field-effect transistor. A feedback circuit is employed to keep the drain current constant by adjusting the voltage applied to the electrolyte (top gate). In the case of DNA, the electrolyte potential increases in response to an increase of hybridized DNA and serves as the electrical signal of interest.

Lab-on-a-chip: A self-contained automated DNA hybridization detection system, for example, employs a custom-design CMOS (complementary metal-oxide-semiconductor) integrated circuit to periodically select and measure the sensor signals sequentially at each element in the microarray. Initially, under buffer electrolyte in the absence of biological analyte, the system scans through the entire array, addressing each element via row and column decoders. After introduction of the analyte and following of the appropriate hybridization protocol, the signals are measured periodically. With proper calibration, a greater magnitude of signal change from one sensor to another indicates a greater degree of sequence expression in the input sample. Given a profile of the levels of expression of particular sequences that fingerprint a known bacterium, virus, or genetic disease, the system then provides an assessment, which may also be a medical diagnosis of genetic disease or infection by pathogen.

EXAMPLE 6

The Detection Algorithm

The computer follows a control sequence embedded in permanent memory once the user pushes a START button underneath the LCD readout. The computer sequentially records values of the electrolyte potential unique to each sensor as follows:

The computer selects an array element, RC, by outputting a row word R and column word C. After a transient delay, the decoder outputs logic 1's only on lines X(R) and Y(C), turning on transistors connected to the lines. This allows current to flow through only sensor RC and into the negative terminal (−) of the current-input amplifier. The current through Sensor RC is compared with a reference current generated by diode-connected transistor Mref. If the current through Sensor RC is higher (lower) than the reference current, the amplifier reduces (increase) the electrolyte potential, which will reduces (increase) the current through the sensor until it equals the reference current. After a programmed delay to allow for this equilibrium, the computer will record the electrolyte potential as a digital number, which is generated by the analog-to-digital converter (ADC). An automated baseline measurement is made for each transistor prior to exposure to target analyte and this data is stored on the computer. Hence, by comparing the baseline with the detection signal, the effective threshold voltage shift of the transistor at fixed current due to target capture is accurately measured.

In a similar fashion, the computer sequences through all 96 wells, A1 to H12. The first time the user presses the START button, the information acquired by the computer is stored as reference values. The user then applies a biological protocol to the assay plate and presses START again. The newly acquired measurements are compared with the references values. The LCD readout indicates which wells show an increase in measured values. The readout is compared with a reference chart generated by the user indicating which wells will undergo immobilization.

An analog to digital converters (ADC) is an electronic circuit that converts continuous signals to discrete digital numbers. ADS circuits are well known. See, for example, U.S. Pat. Nos. 6,407,692 and 6,456,223, each of which is incorporated herein in the entirety by reference.

EXAMPLES 7

Extracting Concentrations of Bound Targets

The shift in electrolyte potential is an indicator of how much target molecule has adsorbed on the sensor. In practice, the relation of this potential shift with the concentration of target molecule is obtained empirically through sensor calibration experiments as mentioned above. To understand the response of the present apparatus, a very simple model is offered that correlates the potential shift to the electrical charges adsorbed through total gate capacitance, which is a series of gate oxide capacitance, and electrolyte double layer capacitance. For the particular geometry of carbon nanotube transistor in the present apparatus, the total capacitance is dominated by the gate oxide capacitance, which has a typical value of 50 fF over an active area of about 5×50 μm². This simple capacitance model then predicts that 1 mV potential shift corresponds to a surface concentration of 8.3×10⁶ molecules/cm² for 15 bases DNA. Assuming that the adsorption of the target molecule to the sensor follows Langmuir model, which relates the surface density to volume density through the following formula:

$$C = \frac{\Gamma}{K_A(\Gamma_{max} - \Gamma)} = \frac{\Gamma}{K_A \Gamma_{max}}$$

where Γ is surface concentration, Γmax is surface concentration of maximum coverage, and $K_A$ is empirical proportional constant. In theory $\Gamma_{max} \approx 6 \times 10^{13}$ molecules/cm² for 15 bases DNA, also theoretical $\Gamma_{max}$ is usually much larger than Γ, and $K_A$ is typically taken to be 6×107 M⁻¹, and $K_A$ is typically taken to be 6×10⁷ M⁻¹. Using these numbers, we estimate that the sensitivity of our apparatus is 2.3 picomolar/mV.

EXAMPLE 8

Hand Held Device or Medical PDA

Figure 26:
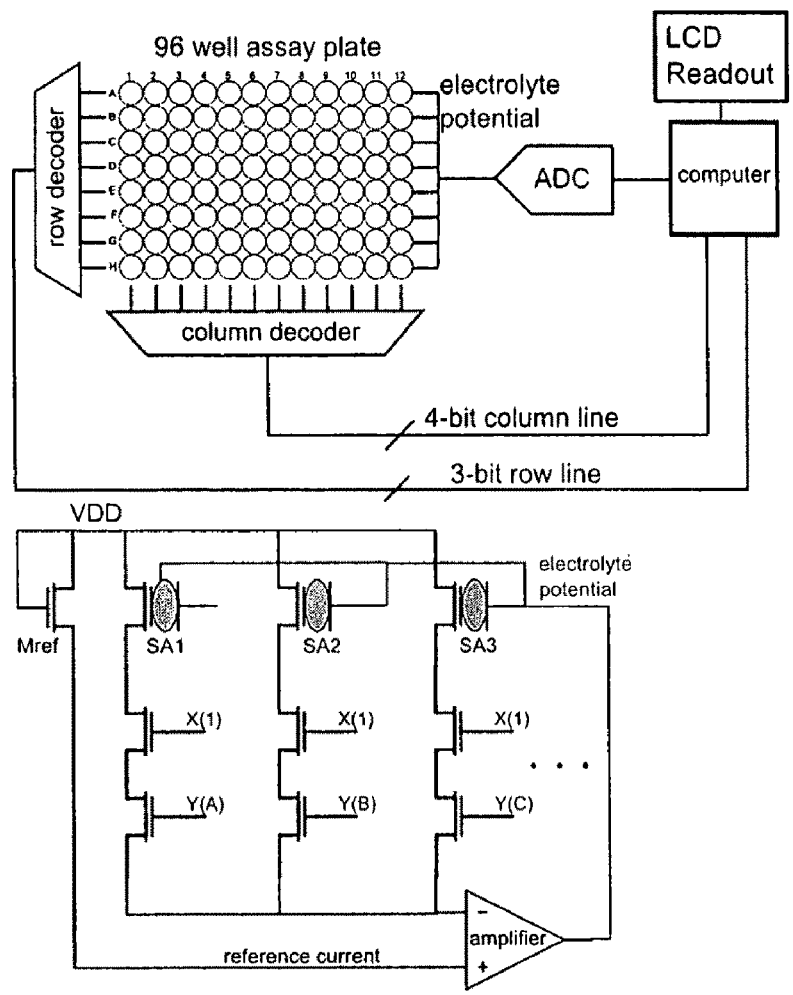
FIG. 26 illustrates an apparatus of the present invention including, by way of example, a 96 well assay plate.

The apparatus of the present invention is also miniaturizable as a medical personal digital assistant (PDA). From FIG. 26, a wireless channel is used between the computer and a remote PDA. Thus, the data acquired from the present apparatus at a lab site, for example, may be sent to an appropriate PDA.

In additional to the probe biological materials listed above, peptide nucleic acids (PNA) may also be used. PNA are widely used in diagnostic assays and antisense therapies. PNAs are advantageous in that due to the higher binding strength of PNA/DNA strands (both single and double) than DNA/DNA strands, it is not necessary to design long PNA oligomers for such uses, whereas oligonucleotide probes of 20-25 mer are commonly required therefore. See U.S. Pat. Nos. 5,582,985; 5,773,571; 6,015,710; 5,786,461 and 6,472,209, each of which is incorporated herein in the entirety by reference.

While the foregoing specification teaches the principles of the present invention, with examples provided for the purpose of illustration, it will be appreciated by one skilled in the art from reading this disclosure that various changes in form and detail can be made without departing from the true scope of the invention.

What is claimed is:

1. An apparatus comprising:
one or more carbon nanotube transistors on a silicon substrate, the one or more carbon nanotube transistors each including a gate electrode, a source electrode, a drain electrode, and a carbon nanotube channel bridging the source electrode and the drain electrode, wherein the drain electrode and the carbon nanotube channel are covered by insulating layer, wherein the insulating layer insulates the drain electrode and the carbon nanotube channel from an electrolyte solution, wherein the gate electrode is configured to contact the electrolyte solution comprising one or more target biological molecules,
one or more specific probe materials immobilized on the insulating layer,
an electronic circuitry to detect a change in electrical charge by each of the one or more carbon nanotube transistors due to binding of the one or more specific probe materials with the one or more target biological molecules,
a detector to detect the change in electrical charge to directly quantify the amount of a bound target biological molecules; and
an automated sensing system for determining a relative abundance of the specific target biological molecule based on the change in electrical charge.

2. The apparatus of claim 1, wherein the one or more carbon nanotube transistors are made by electrically contacting a nanotube mat, and allowing an electrical current to flow through the nanotube mat in proximity to a third electrode separated by an insulating barrier where a voltage applied will cause an electric field to affect the conductance of the one or more carbon nanotube transistors.

3. The apparatus of claim 1, wherein the exposed metallic terminals form the electrical connection to the one or more carbon nanotube transistors.

4. The apparatus of claim 1, wherein the substrate is a glass or a non-conducting polymer.

5. The apparatus of claim 1, wherein the thin insulating layer is an oxide.

6. The apparatus of claim 1, wherein the one or more probe materials are chosen from DNA, RNA, PNA, antibodies, modified antibodies, proteins, peptides, aptamers, and peptide aptamers.

7. The apparatus of claim 1, wherein at least one of the exposed metallic terminals is located on the back side of the substrate.

8. The apparatus of claim 1, wherein the electronic circuitry is external to the at least one of the one or more carbon nanotube transistors.

9. The apparatus of claim 1, wherein the automated sensing system is external to the at least one of the one or more carbon nanotube transistors.

10. The apparatus of claim 1, wherein said at least one of the one or more carbon nanotube transistors is comprised on an array of about 20 to 50 carbon nanotube transistors.

11. The apparatus of claim 1, wherein the carbon nanotube channel bridges a gap between the source and the drain electrodes.

12. The apparatus of claim 1, wherein the multiplicity of specific probe materials comprise cell surface receptor sequences.

13. The apparatus of claim 1, wherein the drain electrode is gold.

14. The apparatus of claim 1, wherein a separation distance between the source and drain electrode is about 5 nm.

15. The apparatus of claim 1, further comprising:
a gate oxide on top of a drain source gap to avoid an electrolyte current leakage, wherein the gate oxide is not insulated by the thin insulating oxide or the nitride layer.

16. The apparatus of claim 15, wherein the gate oxide is an aluminum oxide.

17. The apparatus of claim 16, wherein the aluminum oxide is about 100 nm thick.

18. The apparatus of claim 1, wherein the specific probe materials are immobilized on the insulating oxide or the nitride layer by silane functionalization.

19. The apparatus of claim 18, wherein the silane functionalization comprises MPTMS coupled to a hydroxylated surface of the thin insulating oxide or the nitride layer.

20. A method of electronically detecting a target biological material in a mixture containing the target biological material and other biological materials, which comprises:
a) exposing the mixture containing the target biological material and other biological materials to the at least one chip of the apparatus of claim 1; and
b) determining an absolute amount of the target biological material in the mixture by a change in electrical charge due to binding of the target biological material to a probe material on said at least one chip.

21. The method of claim 20, which further comprises electronically determining a relative abundance of target biological materials in a mixture comprising more than one target biological material.

22. The method of claim 20, wherein the apparatus comprises one chip.

23. The method of claim 20, wherein the target biological material is DNA.

24. The method of claim 20, wherein the target biological material is RNA.

25. The method of claim 24, wherein the RNA is miRNA.

26. The method of claim 20, wherein the probe material is DNA, RNA or PNA.

27. The apparatus of claim 1, wherein the insulating layer comprises a thin insulating oxide or a nitride.

28. The apparatus of claim 27, wherein the thin insulating layer includes exposed metallic terminals for providing electrical conductivity.

* * * * *

SEQUENCE LISTING

```
<160> NUMBER OF SEQ ID NOS: 2

<210> SEQ ID NO 1
<211> LENGTH: 15
<212> TYPE: DNA
<213> ORGANISM: Artificial Sequence
<220> FEATURE:
<223> OTHER INFORMATION: chemically synthesized oligonucleotide probe

<400> SEQUENCE: 1
atccttatca atatt                                                    15
```

-continued

```
<210> SEQ ID NO 2
<211> LENGTH: 15
<212> TYPE: DNA
<213> ORGANISM: Artificial Sequence
<220> FEATURE:
<223> OTHER INFORMATION: chemically synthesized oligonucleotide probe

<400> SEQUENCE: 2
aatattgata aggat                                                     15
```